US010940512B2

(12) United States Patent
Muller et al.

(10) Patent No.: US 10,940,512 B2
(45) Date of Patent: Mar. 9, 2021

(54) TESTING SUBTERRANEAN WATER FOR A HAZARDOUS WASTE MATERIAL REPOSITORY

(71) Applicant: Deep Isolation, Inc., Berkeley, CA (US)

(72) Inventors: Richard A. Muller, Berkeley, CA (US); John Linus Grimsich, Berkeley, CA (US)

(73) Assignee: Deep Isolation, Inc., Berkeley, CA (US)

( * ) Notice: Subject to any disclaimer, the term of this patent is extended or adjusted under 35 U.S.C. 154(b) by 0 days.

(21) Appl. No.: 17/028,667

(22) Filed: Sep. 22, 2020

(65) Prior Publication Data

US 2021/0041410 A1 Feb. 11, 2021

Related U.S. Application Data

(62) Division of application No. 16/796,798, filed on Feb. 20, 2020.

(Continued)

(51) Int. Cl.
   *B09B 1/00* (2006.01)
   *G21F 9/34* (2006.01)
   (Continued)

(52) U.S. Cl.
   CPC .......... *B09B 1/008* (2013.01); *G21F 9/34* (2013.01); *G01N 1/08* (2013.01); *G01N 33/0036* (2013.01); *G01T 1/167* (2013.01)

(58) Field of Classification Search
   CPC .............. B09B 1/008; G21F 9/34; G01N 1/08
   See application file for complete search history.

(56) References Cited

U.S. PATENT DOCUMENTS 4,844,807 A 7/1989 Manchak
5,165,235 A 11/1992 Nitschke
(Continued)

FOREIGN PATENT DOCUMENTS

EP  1394814  3/2004
WO WO 92007667  5/1992
(Continued)

OTHER PUBLICATIONS

[No Author] World Nuclear News, "Yucca Mountain cost estimate rises to $96 billion", Aug. 6, 2008, 2 pages, ISSN 2040-5766.
(Continued)

*Primary Examiner* — Janine M Kreck
(74) *Attorney, Agent, or Firm* — Fish & Richardson P.C.

(57) ABSTRACT

Techniques for determining the suitability of a subterranean formation as a hazardous waste repository include determining a neutron flux of a first isotope in a subterranean formation; calculating, based at least in part on the determined neutron flux of the first isotope, a predicted production rate of a second isotope in the subterranean formation; calculating a first ratio of the predicted production rate of the second isotope relative to a theoretical production rate of a stable form of the second isotope; measuring respective concentrations of the second isotope and the stable form of the second isotope in a subterranean water sample; calculating a second ratio of the measured concentration of the second isotope relative to the measured concentration of the stable form of the second isotope; and based on a comparison of the first and second ratios, determining that the subterranean formation is suitable as a hazardous waste repository.

20 Claims, 11 Drawing Sheets

Related U.S. Application Data

(60) Provisional application No. 62/934,894, filed on Nov. 13, 2019, provisional application No. 62/833,285, filed on Apr. 12, 2019, provisional application No. 62/911,560, filed on Oct. 7, 2019, provisional application No. 62/808,523, filed on Feb. 21, 2019.

(51) Int. Cl.
*G01N 33/00* (2006.01)
*G01N 1/08* (2006.01)
*G01T 1/167* (2006.01)

(56) References Cited

U.S. PATENT DOCUMENTS

| | | | |
|---|---|---|---|
| 5,340,235 | A | 8/1994 | Milliken |
| 5,377,104 | A | 12/1994 | Sorrells et al. |
| 5,387,741 | A | 2/1995 | Shuttle |
| 5,850,614 | A | 12/1998 | Crichlow |
| 5,863,283 | A | 1/1999 | Gardes |
| 6,238,138 | B1 | 5/2001 | Crichlow |
| 7,287,934 | B2 | 10/2007 | Okutsu et al. |
| 8,933,289 | B2 * | 1/2015 | Crichlow .............. G21F 9/34 588/17 |
| 9,921,158 | B2 * | 3/2018 | Rider .............. G01N 21/6428 |
| 10,002,683 | B2 | 6/2018 | Muller et al. |
| 10,315,238 | B1 * | 6/2019 | Muller .............. G01T 1/169 |
| 10,434,550 | B1 | 10/2019 | Muller |
| 2002/0020528 | A1 | 2/2002 | McCabe et al. |
| 2004/0247396 | A1 | 12/2004 | Okutsu et al. |
| 2010/0105975 | A1 | 4/2010 | Baird |
| 2011/0005762 | A1 | 1/2011 | Poole |
| 2013/0214143 | A1 | 8/2013 | Lu et al. |
| 2014/0260528 | A1 | 9/2014 | Schoell |
| 2017/0186505 | A1 | 6/2017 | Muller et al. |
| 2018/0182505 | A1 | 6/2018 | Diefenbach |
| 2020/0271632 | A1 | 8/2020 | Muller et al. |

FOREIGN PATENT DOCUMENTS

| | | |
|---|---|---|
| WO | WO 2013023299 | 2/2013 |
| WO | WO 2015069300 | 5/2015 |
| WO | WO 2016177876 | 11/2016 |
| WO | WO 2018-226636 | 12/2018 |

OTHER PUBLICATIONS

Arnold, et al., "Reference Design and Operations of Deep Borehole Disposal of High-Level Radioactive Waste," Sandia National Laboratories (2011) ("Sandia Report") (available at: http://prod.sandia.gov/techlib/access-control.cgi/2011/116749.pdf), 68 pages.

Cornwall, W., "Deep Sleep. Boreholes drilled into Earth's crust get a fresh look for nuclear waste disposal," Science, vol. 349, Issue 6244, Jul. 10, 2015, pp. 132-135.

Dozier, "Feasibility of Very Deep Borehole Disposal of US Nuclear Defense Wastes," Massachusetts Institute of Technology, Sep. 2011, pp. 1-12.

Faybishenko et al., Editors, Lawrence Berkeley National Laboratory and Sandia National Laboratories: "International Approaches for Deep Geological Disposal of Nuclear Waste: Geological Challenges in Radioactive Waste Isolation", prepared for the US Department of Energy, Fifth Worldwide Review—2016, 474 pages.

Gibb et al., "A Model for Heat Flow in Deep Borehole Disposals of High-Level Nuclear Waste," Journal of Geophysical Research, vol. 113, dated May 6, 2008, 18 pages.

Gibbs, "Feasibility of Lateral Emplacement in Very Deep Borehole Disposal of High Level Nuclear Waste" master's thesis, Massachusetts Institute of Technology (2010) ("Gibbs") (available at: https://dspace.mit.edu/handle/1721.1/63242), 2 pages.

Hama et al., "Groundwater dating applied for geological disposal of radioactive waste—A review of methods employed worldwide," J. Jap. Assoc. Hydrol. Sci., 2014, 44(1):39-64.

Hoag, "Canister Design for Deep Borehole Disposal of Nuclear Waste," Massachusetts Institute of Technology, May 2006, pp. 1-6.

Muller, R. "Radioisotope Dating with a Cyclotron," Science, vol. 196, No. 4289, dated Apr. 29, 1977, 6 pages.

Nakata et al., "An Evaluation of the Long-Term Stagnancy of Porewater in the Neogene Sedimentary Rocks in Northern Japan," Geofluids, 2018, 21 pages, doi.org/10.1155/2018/7823195.

Neuzil et al., "Shale: An overlooked option for US nuclear waste disposal," Bulletin of the Atomic Scientists Nov. 2014, Retrieved fro: URL<http://thebulletin.org/shale-overlooked-option-us-nuclear-waste-disposal17831>, printed Sep. 26, 2016, 5 pages.

Neuzil, "Can Shale Safely Host U.S. Nuclear Waste?" EOS, vol. 94, No. 30, dated Jul. 23, 2013, 3 pages.

PCT International Search Report and Written Opinion in International Application No. PCT/US2019/059883, dated Feb. 19, 2020, 13 pages.

PCT International Search Report and Written Opinion issued in International Application No. PCT/US2016/066539, dated Apr. 19, 2017, 13 pages.

PCT Notification of Transmittal of the International Search Report and Written Opinion in International Application No. PCT/US2018/035974, dated Aug. 24, 2018, 13 pages.

Sone et al., "Mechanical properties of shale-gas reservoir rocks—Part 1: Static and dynamic elastic properties and anisotropy," Geophysics, vol. 78, No. 5, Sep.-Oct. 2013, D381-92, 12 pages.

U.S. Nuclear Waste Technical Review Board, "A Report to the U.S. Congress and the Secretary of Energy, Evaluation of Technical Issues Associated With the Development of a Separate Repository for U.S. Department of Energy-Managed High-Level Radioactive Waste and Spent Nuclear Fuel," (2015) ("NWTRB") (available at: http://www.nwtrb.gov/reports/disposal_options.pdf).

Vartabedian, "Decades-old war over Yucca Mountain nuclear dump resumes under Trump budget plan," Mar. 29, 2017, ralph.vartabdian@latimes.com; twitter @rvartabedian; 4 pages.

Wikipedia.org [online], "Dye Tracing," Jul. 30, 2019, retrieved on Jan. 25, 2020, retrieved from URL <https://en.wikipedia.org/wiki/Dye_tracing>, 3 pages.

Wikipedia.org [online], "Accelerator Mass Spectrometry," Apr. 9, 2018, retrieved on Aug. 27, 2018, retrieved from URL <http://en.wikipedia.org/wiki/Accelerator_mass_spectrometry>, 3 pages.

Winterle et al., "Regulatory Perspectives on Deep Borehole Disposal Concepts," prepared for the U.S. Nuclear Regulatory Commission, Contract NRC-02-07006, Center for Nuclear Waste. Regulatory Analyses, San Antonio, TX, May 2011, 24 pages.

YuccaMountain.org; Eureka County, Nevada—Nuclear Waste Office, FAQ, Eureka County Home, last updated Mar. 17, 2017, 12 pages.

PCT International Search Report and Written Opinion in International Appln. No. PCT/US2020/019231, dated Oct. 30, 2020, 9 pages.

* cited by examiner

TESTING SUBTERRANEAN WATER FOR A HAZARDOUS WASTE MATERIAL REPOSITORY

CROSS-REFERENCE TO RELATED APPLICATION

This application is a divisional of and claims priority to U.S. patent application Ser. No. 16/796,798, filed on Feb. 20, 2020, and entitled "TESTING SUBTERRANEAN WATER FOR A HAZARDOUS WASTE MATERIAL REPOSITORY," which in turn claims priority under 35 U.S.C. § 119 to: U.S. Provisional Patent Application Ser. No. 62/808,523, filed on Feb. 21, 2019; U.S. Provisional Patent Application Ser. No. 62/833,285, filed on Apr. 12, 2019; U.S. Provisional Patent Application Ser. No. 62/911,560, filed on Oct. 7, 2019; and U.S. Provisional Patent Application Ser. No. 62/934,894, filed on Nov. 13, 2019. The entire contents of each of the previous applications are incorporated by reference herein.

TECHNICAL FIELD

This disclosure relates to testing subterranean water and, more particular, testing subterranean water for one or more radioactive isotopes for a hazardous waste material repository.

BACKGROUND

Storing hazardous waste material underground may have significant risks. One risk may be that the hazardous waste material, or byproducts of the hazardous waste material, may enter into a source of human-consumable water. Some subterranean formations allow mobile water; that is the movement of water stored in the formation to a location in which human-consumable water is located. Therefore, any hazardous waste material stored underground must be kept from a source of mobile water.

SUMMARY

In a general implementation, a method includes determining a concentration of at least one noble gas isotope of a plurality of noble gas isotopes in fluid sample from a subterranean formation below a terranean surface; determining a produced amount of the at least one noble gas isotope in the subterranean formation based on a production rate of the at least one noble gas isotope and a minimum residence time; calculating a ratio of the determined concentration of the at least one noble gas isotope in the fluid sample to the determined produced amount of the at least one noble gas isotope; and based on the calculated ratio being at or near a threshold value, determining that the subterranean formation is suitable as a hazardous waste repository.

In an aspect combinable with the general implementation, the production rate is based on one or more properties of rock in the subterranean formation.

In another aspect combinable with any of the previous aspects, the one or more properties include a bulk rock chemistry of the subterranean formation.

In another aspect combinable with any of the previous aspects, the one or more properties include an amount of uranium or thorium, or both, per unit volume in the subterranean formation.

In another aspect combinable with any of the previous aspects, the one or more properties include a decay rate of uranium or thorium, or both, in the subterranean formation.

In another aspect combinable with any of the previous aspects, the at least one noble gas isotope includes at least one of helium (He), neon (Ne), argon (Ar), krypton (Kr), or xenon (Xe).

Another aspect combinable with any of the previous aspects further includes determining a concentration of another noble gas isotope of the plurality of noble gas isotopes in a fluid sample from a subterranean formation below a terranean surface; determining a produced amount of the another noble gas isotope in the subterranean formation based on a production rate of the another noble gas isotope and a minimum residence time that is sufficient to show that the subterranean formation is suitable as a hazardous waste repository; calculating another ratio of the determined concentration of the another noble gas isotope in the water sample to the determined produced amount of the another noble gas isotope; and based on the another calculated ratio being at or near a threshold value, determining that the subterranean formation is suitable as the hazardous waste repository.

Another aspect combinable with any of the previous aspects further includes comparing the calculated ratio with the another calculated ratio; and based on the comparison, determining that the subterranean formation is suitable as the hazardous waste repository.

In another aspect combinable with any of the previous aspects, the at least one noble gas isotope is produced from a first production mode, and the another noble gas isotope is produced from a second production mode different than the first production mode.

Another aspect combinable with any of the previous aspects further includes collecting the water sample from a drillhole formed into the subterranean formation.

In another aspect combinable with any of the previous aspects, collecting the water sample includes operating a downhole tool in the drillhole to collect a core sample from the subterranean formation; retrieving the core sample to the terranean surface; and removing the water sample from the core sample.

Another aspect combinable with any of the previous aspects further includes forming the drillhole from the terranean surface to the subterranean formation.

In another aspect combinable with any of the previous aspects, the drillhole includes a vertical drillhole.

In another aspect combinable with any of the previous aspects, the subterranean formation includes a shale formation.

In another aspect combinable with any of the previous aspects, the subterranean formation includes an impermeable layer.

In another aspect combinable with any of the previous aspects, the minimum residence time is at least 10,000.

In another aspect combinable with any of the previous aspects, the threshold value is one.

Another aspect combinable with any of the previous aspects further includes initiating creation of the hazardous waste repository in or under the subterranean formation.

In another aspect combinable with any of the previous aspects, initiating creation of the hazardous waste repository in or under the subterranean formation includes forming an access drillhole from the terranean surface toward the subterranean formation; and forming a storage drillhole coupled to the access drillhole in or under the subterranean formation, the storage drillhole including a hazardous waste storage area.

In another aspect combinable with any of the previous aspects, the access drillhole includes a vertical drillhole.

In another aspect combinable with any of the previous aspects, the drillhole includes a portion of the access drillhole.

In another aspect combinable with any of the previous aspects, the storage drillhole includes a curved portion and a horizontal portion.

In another aspect combinable with any of the previous aspects, the subterranean formation includes a thickness proximate the hazardous waste storage area of at least about 200 feet.

In another aspect combinable with any of the previous aspects, the subterranean formation includes a thickness proximate the hazardous waste storage area that inhibits diffusion of a hazardous waste material through the subterranean formation for an amount of time that is based on a half-life of the hazardous waste material.

Another aspect combinable with any of the previous aspects further includes installing a casing in the access drillhole and the storage drillhole that extends from at or proximate the terranean surface, through the access drillhole and the storage drillhole, and into the hazardous waste storage area of the storage drillhole.

Another aspect combinable with any of the previous aspects further includes cementing the casing to the access drillhole and the storage drillhole.

Another aspect combinable with any of the previous aspects further includes, subsequent to forming the access drillhole, producing hydrocarbon fluid from the subterranean formation, through the access drillhole, and to the terranean surface.

Another aspect combinable with any of the previous aspects further includes storing hazardous waste material in the hazardous waste storage area.

In another aspect combinable with any of the previous aspects, storing hazardous waste material in the hazardous waste storage area includes moving a storage canister through an entry of the access drillhole that extends into the terranean surface, the entry at least proximate the terranean surface, the storage canister including an inner cavity sized to enclose the hazardous waste material; moving the storage canister through the access drillhole and into the storage drillhole; and moving the storage canister through the storage drillhole to the hazardous waste storage area.

Another aspect combinable with any of the previous aspects further includes forming a seal in at least one of the access drillhole or the storage drillhole that isolates the hazardous waste storage area from the entry of the access drillhole.

In another aspect combinable with any of the previous aspects, the hazardous waste material includes spent nuclear fuel.

In another aspect combinable with any of the previous aspects, the storage canister includes a connecting portion configured to couple to at least one of a downhole tool string or another storage canister.

Another aspect combinable with any of the previous aspects further includes monitoring the hazardous waste material stored in the hazardous waste storage area.

In another aspect combinable with any of the previous aspects, monitoring the hazardous waste material stored in the hazardous waste storage area includes removing the seal; and retrieving the storage canister from the hazardous waste storage area to the terranean surface.

In another aspect combinable with any of the previous aspects, monitoring the hazardous waste material stored in the hazardous waste storage area of the storage drillhole includes monitoring at least one variable associated with the storage canister from a sensor positioned proximate the hazardous waste storage area; and recording the monitored variable at the terranean surface.

In another aspect combinable with any of the previous aspects, the monitored variable includes at least one of radiation level, temperature, pressure, presence of oxygen, presence of water vapor, presence of liquid water, acidity, or seismic activity.

Another aspect combinable with any of the previous aspects further includes, based on the monitored variable exceeding a threshold value, removing the seal; and retrieving the storage canister from the hazardous waste storage area to the terranean surface.

In another aspect combinable with any of the previous aspects, the fluid sample includes liquid brine.

In another aspect combinable with any of the previous aspects, the minimum residence time is sufficient to show that the subterranean formation is suitable as the hazardous waste repository.

In another general implementation, a method includes calculating a concentration of a krypton isotope in a subterranean water sample collected from a subterranean formation; determining that the concentration of the krypton isotope is less than a threshold value; and based on the determination, determining that the subterranean formation is suitable as a hazardous waste repository.

In an aspect combinable with the general implementation, the krypton isotope is Kr-81.

In another aspect combinable with any of the previous aspects, calculating includes using Atom Trap Trace Analysis to calculate the concentration of the krypton isotope.

In another aspect combinable with any of the previous aspects, the threshold value is based on a concentration of the krypton isotope in a surface water sample.

In another aspect combinable with any of the previous aspects, the threshold value is between 16-20 atoms of the krypton isotope in the subterranean water sample.

Another aspect combinable with any of the previous aspects further includes collecting the subterranean water sample from a drillhole formed into the subterranean formation.

In another aspect combinable with any of the previous aspects, collecting the subterranean water sample includes operating a downhole tool in the drillhole to collect a core sample from the subterranean formation; retrieving the core sample to the terranean surface; and removing the subterranean water sample from the core sample.

Another aspect combinable with any of the previous aspects further includes forming the drillhole from the terranean surface to the subterranean formation.

In another aspect combinable with any of the previous aspects, the drillhole includes a vertical drillhole.

In another aspect combinable with any of the previous aspects, the subterranean formation includes a shale formation.

In another aspect combinable with any of the previous aspects, the subterranean formation includes an impermeable layer.

Another aspect combinable with any of the previous aspects further includes initiating creation of the hazardous waste repository in or under the subterranean formation.

In another aspect combinable with any of the previous aspects, initiating creation of the hazardous waste repository in or under the subterranean formation includes forming an access drillhole from the terranean surface toward the subterranean formation; and forming a storage drillhole coupled to the access drillhole in or under the subterranean formation, the storage drillhole including a hazardous waste storage area.

In another aspect combinable with any of the previous aspects, the access drillhole includes a vertical drillhole.

In another aspect combinable with any of the previous aspects, the drillhole includes a portion of the access drillhole.

In another aspect combinable with any of the previous aspects, the storage drillhole includes a curved portion and a horizontal portion.

In another aspect combinable with any of the previous aspects, the subterranean formation includes a thickness proximate the hazardous waste storage area of at least about 200 feet.

In another aspect combinable with any of the previous aspects, the subterranean formation includes a thickness proximate the hazardous waste storage area that inhibits diffusion of a hazardous waste material through the subterranean formation for an amount of time that is based on a half-life of the hazardous waste material.

Another aspect combinable with any of the previous aspects further includes installing a casing in the access drillhole and the storage drillhole that extends from at or proximate the terranean surface, through the access drillhole and the storage drillhole, and into the hazardous waste storage area of the storage drillhole.

Another aspect combinable with any of the previous aspects further includes cementing the casing to the access drillhole and the storage drillhole.

Another aspect combinable with any of the previous aspects further includes, subsequent to forming the access drillhole, producing hydrocarbon fluid from the subterranean formation, through the access drillhole, and to the terranean surface.

Another aspect combinable with any of the previous aspects further includes storing hazardous waste material in the hazardous waste storage area.

In another aspect combinable with any of the previous aspects, storing hazardous waste material in the hazardous waste storage area includes moving a storage canister through an entry of the access drillhole that extends into the terranean surface, the entry at least proximate the terranean surface, the storage canister including an inner cavity sized to enclose the hazardous waste material; moving the storage canister through the access drillhole and into the storage drillhole; and moving the storage canister through the storage drillhole to the hazardous waste storage area.

Another aspect combinable with any of the previous aspects further includes forming a seal in at least one of the access drillhole or the storage drillhole that isolates the hazardous waste storage area from the entry of the access drillhole.

In another aspect combinable with any of the previous aspects, the hazardous waste material includes spent nuclear fuel.

In another aspect combinable with any of the previous aspects, the storage canister includes a connecting portion configured to couple to at least one of a downhole tool string or another storage canister.

Another aspect combinable with any of the previous aspects further includes monitoring the hazardous waste material stored in the hazardous waste storage area.

In another aspect combinable with any of the previous aspects, monitoring the hazardous waste material stored in the hazardous waste storage area includes removing the seal; and retrieving the storage canister from the hazardous waste storage area to the terranean surface.

In another aspect combinable with any of the previous aspects, monitoring the hazardous waste material stored in the hazardous waste storage area of the storage drillhole includes monitoring at least one variable associated with the storage canister from a sensor positioned proximate the hazardous waste storage area; and recording the monitored variable at the terranean surface.

In another aspect combinable with any of the previous aspects, the monitored variable includes at least one of radiation level, temperature, pressure, presence of oxygen, presence of water vapor, presence of liquid water, acidity, or seismic activity.

Another aspect combinable with any of the previous aspects further includes, based on the monitored variable exceeding a threshold value, removing the seal; and retrieving the storage canister from the hazardous waste storage area to the terranean surface.

In another aspect combinable with any of the previous aspects, the subterranean water sample includes brine.

In another general implementation, a method includes determining a neutron flux of a first isotope in a subterranean formation; calculating, based at least in part on the determined neutron flux of the first isotope, a predicted production rate of a second isotope in the subterranean formation; calculating a first ratio of the predicted production rate of the second isotope relative to a theoretical production rate of a stable form of the second isotope; measuring respective concentrations of the second isotope and the stable form of the second isotope in a subterranean water sample from the subterranean formation; calculating a second ratio of the measured concentration of the second isotope relative to the measured concentration of the stable form of the second isotope; and based on a comparison of the first and second ratios, determining that the subterranean formation is suitable as a hazardous waste repository.

In an aspect combinable with the general implementation, the first isotope includes a first half-life, and the second isotope includes a second half-life longer than the first half-life.

In another aspect combinable with any of the previous aspects, the first isotope includes Ar-39, Fe-59, Co-60, Ni-63, Kr-85, Ni-63, or C-14.

In another aspect combinable with any of the previous aspects, the second isotope includes Cl-36.

In another aspect combinable with any of the previous aspects, the stable form of the second isotope includes Cl-35.

In another aspect combinable with any of the previous aspects, comparing the first and second ratios includes determining that the first and second ratios are equal.

In another aspect combinable with any of the previous aspects, determining the neutron flux of the first isotope includes determining the neutron flux based on a bulk rock chemistry of the subterranean formation.

In another aspect combinable with any of the previous aspects, the bulk rock chemistry includes an amount of uranium or thorium (or both) per unit volume of the subterranean formation.

Another aspect combinable with any of the previous aspects further includes collecting the subterranean water sample from a drillhole formed into the subterranean formation.

In another aspect combinable with any of the previous aspects, collecting the subterranean water sample includes operating a downhole tool in the drillhole to collect a core sample from the subterranean formation; retrieving the core sample to the terranean surface; and removing the subterranean water sample from the core sample.

Another aspect combinable with any of the previous aspects further includes forming the drillhole from the terranean surface to the subterranean formation.

In another aspect combinable with any of the previous aspects, the drillhole includes a vertical drillhole.

In another aspect combinable with any of the previous aspects, the subterranean formation includes a shale formation.

In another aspect combinable with any of the previous aspects, the subterranean formation includes an impermeable layer.

Another aspect combinable with any of the previous aspects further includes initiating creation of the hazardous waste repository in or under the subterranean formation.

In another aspect combinable with any of the previous aspects, initiating creation of the hazardous waste repository in or under the subterranean formation includes forming an access drillhole from the terranean surface toward the subterranean formation; and forming a storage drillhole coupled to the access drillhole in or under the subterranean formation, the storage drillhole including a hazardous waste storage area.

In another aspect combinable with any of the previous aspects, the access drillhole includes a vertical drillhole.

In another aspect combinable with any of the previous aspects, the drillhole includes a portion of the access drillhole.

In another aspect combinable with any of the previous aspects, the storage drillhole includes a curved portion and a horizontal portion.

In another aspect combinable with any of the previous aspects, the subterranean formation includes a thickness proximate the hazardous waste storage area of at least about 200 feet.

In another aspect combinable with any of the previous aspects, the subterranean formation includes a thickness proximate the hazardous waste storage area that inhibits diffusion of a hazardous waste material through the subterranean formation for an amount of time that is based on a half-life of the hazardous waste material.

Another aspect combinable with any of the previous aspects further includes installing a casing in the access drillhole and the storage drillhole that extends from at or proximate the terranean surface, through the access drillhole and the storage drillhole, and into the hazardous waste storage area of the storage drillhole.

Another aspect combinable with any of the previous aspects further includes cementing the casing to the access drillhole and the storage drillhole.

Another aspect combinable with any of the previous aspects further includes, subsequent to forming the access drillhole, producing hydrocarbon fluid from the subterranean formation, through the access drillhole, and to the terranean surface.

Another aspect combinable with any of the previous aspects further includes storing hazardous waste material in the hazardous waste storage area.

In another aspect combinable with any of the previous aspects, storing hazardous waste material in the hazardous waste storage area includes moving a storage canister through an entry of the access drillhole that extends into the terranean surface, the entry at least proximate the terranean surface, the storage canister including an inner cavity sized to enclose the hazardous waste material; moving the storage canister through the access drillhole and into the storage drillhole; and moving the storage canister through the storage drillhole to the hazardous waste storage area.

Another aspect combinable with any of the previous aspects further includes forming a seal in at least one of the access drillhole or the storage drillhole that isolates the hazardous waste storage area from the entry of the access drillhole.

In another aspect combinable with any of the previous aspects, the hazardous waste material includes spent nuclear fuel.

In another aspect combinable with any of the previous aspects, the storage canister includes a connecting portion configured to couple to at least one of a downhole tool string or another storage canister.

Another aspect combinable with any of the previous aspects further includes monitoring the hazardous waste material stored in the hazardous waste storage area.

In another aspect combinable with any of the previous aspects, monitoring the hazardous waste material stored in the hazardous waste storage area includes removing the seal; and retrieving the storage canister from the hazardous waste storage area to the terranean surface.

In another aspect combinable with any of the previous aspects, monitoring the hazardous waste material stored in the hazardous waste storage area of the storage drillhole includes monitoring at least one variable associated with the storage canister from a sensor positioned proximate the hazardous waste storage area; and recording the monitored variable at the terranean surface.

In another aspect combinable with any of the previous aspects, the monitored variable includes at least one of radiation level, temperature, pressure, presence of oxygen, presence of water vapor, presence of liquid water, acidity, or seismic activity.

Another aspect combinable with any of the previous aspects further includes, based on the monitored variable exceeding a threshold value, removing the seal; and retrieving the storage canister from the hazardous waste storage area to the terranean surface.

Implementations of subterranean water testing systems and methods according to the present disclosure may also include one or more of the following features. For example, subterranean water testing systems and methods according to the present disclosure may be used to identify or determine that a particular subterranean formation is suitable as a hazardous waste material repository. The determined hazardous waste material repository may be used to store hazardous waste material, such as spent nuclear fuel, isolated from human-consumable water sources. The determined hazardous waste material repository may be suitable for storing the hazardous waste material for durations of time up to, for example, 1,000,000 years. As another example, subterranean water testing systems and methods according to the present disclosure may confirm that a particular geologic formation is suitable as a hazardous waste material repository.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

Radioactive waste (e.g., spent nuclear fuel, high level waste, or otherwise) includes components that last for thousands to hundreds of thousands of years. The radioactive waste can be disposed of in deep directional drillholes (e.g., human-unoccupiable drillholes or wellbores that are too small for a human to enter or occupy) that form or comprise a hazardous waste repository (also human-unoccupiable) that is formed in a subterranean formation. For example, high-level radioactive waste and other hazardous materials can be disposed in horizontal drillholes. When so disposed, a threat to human safety is that some of the radioactive waste can be dissolved or otherwise incorporated into brines and other water that is often found at the same depth as the stored radioactive waste. The flow of these liquids could carry the radioactive waste to a terranean surface or to aquifers (or other water sources). Because the toxicity of the radioactive waste is long lived, it is desirable that the subterranean formation in which the radioactive waste is stored show that fluids in such formation be demonstrably isolated (e.g., from the terranean surface or water sources) for thousands, to tens of thousands, to hundreds of thousands, to a million years or more.

In some aspects, isolation may be demonstrated by showing that any flow of liquids in such a subterranean formation be extremely slow. For example, if the radioactive waste is disposed at a depth of 1000 meters (m), then a flow of liquid in the formation of 1 millimeter (mm) per year could bring such waste (e.g., dissolved or entrained in the liquid) to the surface in a million years. Current measuring techniques are unable of making direct determination of such tiny flow velocities. As a result, safety for underground disposal is typically demonstrated by measurement of the permeability of the rock at depth, combined with plausible assumptions of driving forces (e.g., pressure gradients in the fluid) to calculate, often with complex computer code, the expected rate of flow of deep fluids to the surface.

An alternative or supplementary technique to estimate isolation can be based on the past history of the rock formation that holds the repository. If the brines or other liquids in the formation can be shown to have persisted in the subterranean formation for, e.g., a million years, without flow toward the terranean surface, then such persistence is evidence of the isolative properties of the subterranean formation, making it a possible location for a hazardous waste repository. Such a determination is based, for example, on the fact that unlike surface features, underground geology changes extremely slowly. Events that are difficult to model, such as creation of new earthquake faults, can be assumed to be no more prevalent in the future than they have been in the past.

Figure 1:
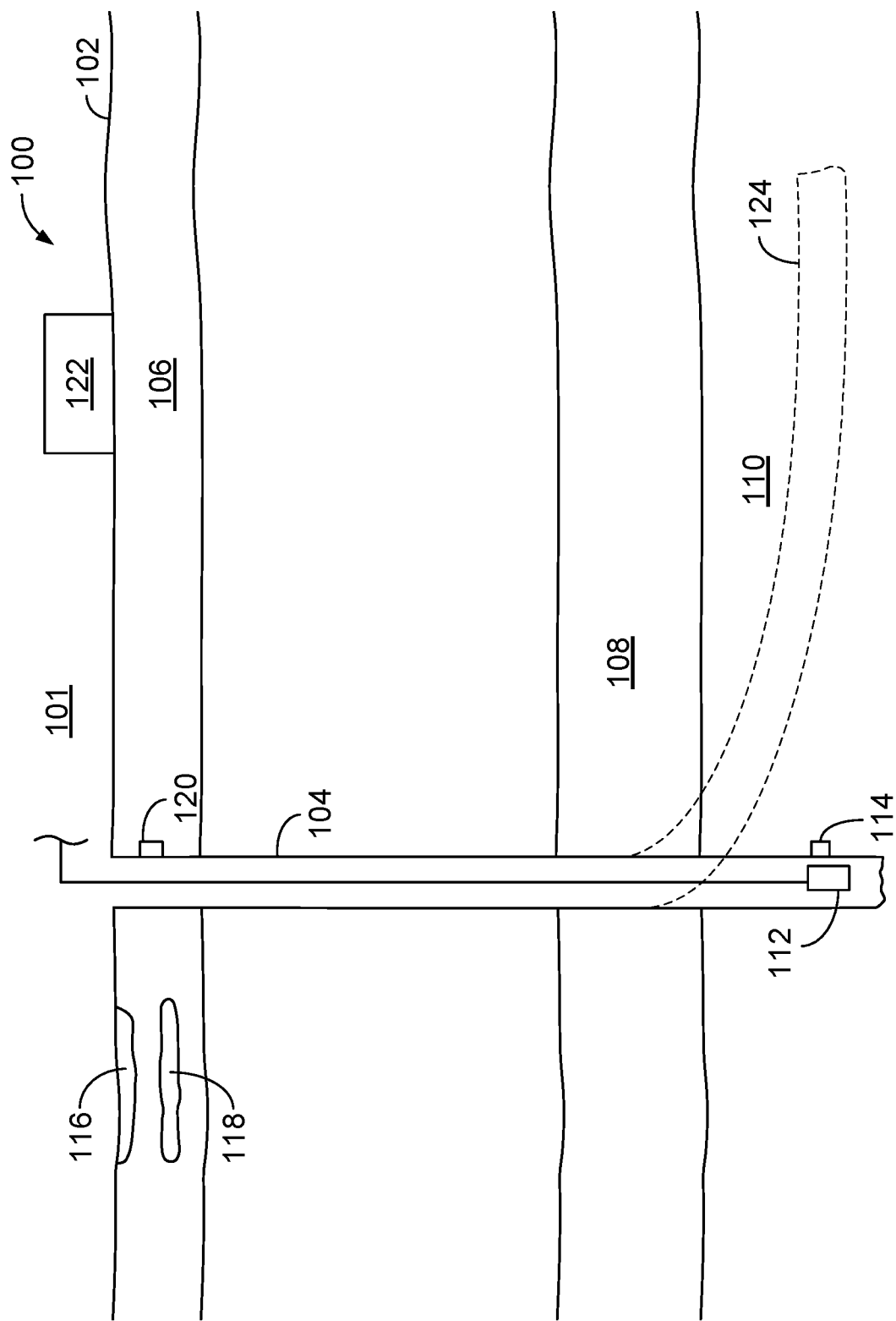
FIG. 1 is a schematic illustration of an example implementation of a subterranean water testing system according to the present disclosure.

FIG. 1 is a schematic illustration of an example implementation of a subterranean water testing system 100. As shown in this example, the system 100 includes a test drillhole 104 formed from a terranean surface 102, through a surface water formation 106, and into and through subterranean formations 108 and 110 that are deeper than the surface water formation 106. Each of the formations 106, 108, and 110 may comprise a geologic formation formed of one or more rock types, as well as water (e.g., fresh or brine) and in some cases other fluids (e.g., hydrocarbon fluids). In this example, the test drillhole 104 is shown as a vertical drillhole. However, in alternative implementations, a directional drillhole 124 (shown in dashed line) may be formed and used in the system 100 in place of (or in addition to) the test drillhole 104) according to the present disclosure.

The test drillhole 104 may be drilled or otherwise formed from the terranean formation to one or both of the subterranean formations 108 or 110 (as well as formations shallower than or deeper than one or both of the formations 108 or 110). Test drillhole 104, may be relatively smaller (e.g., in diameter) than a wellbore formed for the purpose of producing hydrocarbons. Alternatively, test drillhole 104 may be similar to a wellbore formed for the purpose of producing hydrocarbon and, in some aspects, may have had hydrocarbons produced therefrom.

The surface water formation 106, in this example, is a geologic layer comprised of one or more layered rock formations and includes one or more surface water sources. For example, surface water formation 106 may include one or more open water sources 116 (e.g., lakes, ponds, rivers, creeks). In some aspects, open water sources 116 are water sources that have direct contact with the atmosphere 101. Surface water formation 106 may also include one or more aquifers 118 that are not in direct contact with the atmosphere 101 but are suitable for human consumption (e.g., with or without conventional water treatment). Thus, in this example implementation of system 100, surface water includes both open water sources 116 and aquifers 118. Examples of rock formations of which the surface water formation 106 may be composed include porous sandstones and limestones, among other formations.

Below the surface water formation 106, in this example implementation, are subterranean formations 108 and 110. One or both of the subterranean formations 108 or 110 may include or hold subterranean water. Subterranean water, in this example system, is water that is not an open water source or aquifer and is not in present-day contact with the atmosphere 101 (but may have been at some time in the past). In some aspects, subterranean water is non-potable or is not fit for human consumption (or both). System 100 may be used (e.g., as described with reference to FIG. 3 and process 300) to test one or both of subterranean formations 108 or 110 for hazardous waste material storage according to the subterranean water found in such formations.

System 100 also includes a downhole tool 112 (e.g., a core drill) that can be conveyed into the test drillhole 104 and to one or all of formations 106, 108, and 110 to procure a core sample 114 or core sample 120. In this example, core sample 114 include subterranean water while core sample 120 includes surface water. Thus, a subterranean water sample may be obtained from core sample 114, while a surface water sample may be obtained from core sample 120 (or open water source 116 or aquifer 118). Although core sample 114 is shown as being obtained from subterranean formation 110, one or more core samples 114 may be obtained from this formation or subterranean formation 108 (or both).

System 100 also includes a subterranean water (or other fluid) testing system, represented schematically as testing system 122. As described in more detail herein, the testing system 122 may perform one or more tests on, e.g., a subterranean fluid (e.g., water such as brine) sample and, in some aspects, a surface fluid (e.g., water or other liquid) sample. As described more specifically herein, the testing system 122 may be, in some aspects, a processor-based control system that testes the subterranean fluid sample (and in some aspects, the surface fluid sample) for the presence, or concentration, of one or more radioisotopes (stable or otherwise) within the sample(s).

In an example implementation, the fluid testing system 122 includes an accelerator mass spectrometry system (AMS). The AMS system, generally, may be operated to perform many testing functions. For example, the AMS system may analyze substances, such as water, to detect naturally occurring, long-lived radio-isotopes (of elements) such as beryllium-10 ($^{10}Be$), chlorine-36 ($^{36}Cl$), aluminum-26 ($^{26}Al$), iodine-129 ($^{129}I$) and carbon-14 (i.e., radiocarbon or $^{14}C$) in such substances. In some cases, certain radioactive isotopes, such as $^{36}Cl$ and $^{129}I$, may be produced in the atmosphere 101 by cosmic radiation, and mixed with surface water, or is produced directly in the surface water or surface rock. Thus, substances such as surface water sources may have a particular concentration of such radioactive isotopes of the elements based on time period of the atmosphere 101 to which the substances have been exposed. Substances no longer exposed to the atmosphere 101, such as subterranean water, experience a decay in the concentration of such radioactive isotopes (e.g., $^{36}Cl$ relative to the concentration of the stable isotope, $^{37}Cl$, of the element chlorine; $^{129}I$ relative to the concentration of the stable isotope, $^{127}I$, of the element iodine; $^{10}Be$ relative to the concentration of the stable isotope, $^{9}Be$, of the element beryllium; $^{14}C$ relative to the concentration of the stable isotopes, $^{12}C$ or $^{13}C$, of the element carbon; $^{26}Al$ relative to the concentration of the stable isotope, $^{27}Al$, of the element aluminum) as time passes without such exposure. Thus, a measure of a concentration of radioactive isotopes in a substance, such as subterranean water, may also indicate an amount of time that has passed since the substance was last exposed to the atmosphere 101 or surface water.

In an example operation of the system 100 including an AMS as the fluid testing system 122 (or part of the system 122), a subterranean water sample may be collected from the drillhole 104 (or from a core sample from one or both of the subterranean formations 108 and 110). "Collecting" may include or mean identifying a previously gathered subterranean water sample. A surface water sample may also be collected from a surface water source. "Collecting" may include or mean identifying a previously gathered subterranean water sample, or identifying a previously determined value of the concentration of the radioactive isotope relative to the stable isotope of the element in the surface water. A concentration of the radioactive isotope (such as $^{129}I$) compared to that of the stable isotope (for this case, $^{127}I$) can be determined from prior measurements, e.g., prior to the execution of process 300) of these ratios taken from surface water. The AMS system determines a concentration of a radioactive isotope in the subterranean water sample. For example, the AMS system may be operated to determine a concentration of a particular radioactive isotope, such as $^{36}Cl$ or $^{129}I$ (or both), in the subterranean water sample (e.g., relative to a corresponding stable isotope of that element). In some aspects, this may also include include determining the concentration of the particular radioactive isotope in the surface water sample as well. Alternatively, the concentration of the radioactive isotope in the surface water sample may be known. The determination of the concentration of the radioactive isotope with the AMS system may include measuring a ratio of the radioactive isotope (e.g., $^{36}Cl$ or $^{129}I$) in the particular water sample to a stable (non-radioactive) isotope (e.g., $^{35}Cl$ or $^{127}I$) of the same element (chlorine or iodine, respectively). Thus, reference to determining a concentration of the radioactive element means, in some aspects, determining a ratio of the radioactive isotope to the stable (non-radioactive) isotope of the same element in the particular (surface or subterranean, or both) sample. The AMS system may then compare the concentrations of the radioactive isotope in the subterranean water sample and the surface water sample. Based on the comparison, the AMS system may be used to determine (at least in part) that the subterranean formation is suitable as a hazardous waste storage repository. For example, criteria for determining that the subterranean formation (108 or 110 or both) is suitable for the long-term (e.g., 100, 1000, 10,000 years or more) storage of hazardous waste material (e.g., spent nuclear fuel) may be the presence of water that has not been exposed to the atmosphere 101 for a particular duration of time, thereby evidencing the subterranean formation as a geologic formation which does not permit mobile water therethrough, or otherwise allow a flow of liquid from the formation toward the surface water formation 106. Such evidence may be proof of the subterranean formation to store hazardous waste material with little to no chance of such material mixing or polluting potable water fit for human consumption at the surface water formation 106. Based on that determination, the hazardous waste storage repository may be created (or creation may be initiated) in or under the subterranean formation (108 or 110 or both).

The present disclosure also describes example implementations of systems and methods for determining that a subterranean formation (e.g., formation 108 or 110, both, or another subterranean formation) is suitable as a hazardous (e.g., nuclear or radioactive) waste repository formed in deep, human-unoccupiable directional drillholes based on a determination that fluids (e.g., water, brines, and gases) have been essentially stagnant in the subterranean formation for periods of tens of thousands to millions of years. For example, when brines in a geologic environment (such as a subterranean formation) are stagnant for long periods of time and isolated from surface waters, a number of geochemical, biological, radiogenic and nucleogenic markers can develop within the isolated waters that provide independent and corroborating evidence for the stagnancy and isolation of the brine. Used in combination, these markers can provide a compelling and internally self-checking system of assessing the suitability of a subterranean formation for use as a hazardous waste repository formed in deep, directional drillholes.

As an example, there may be indirect indicators of long-term (e.g., hundreds, to thousands, to tens of thousands, to millions of years) isolation of a fluid (e.g., brine liquid) in a particular subterranean formation. In some cases, such indirect markers provide evidence for physical isolation of brines without providing explicit age estimates for the duration of brine isolation. Nonetheless, these markers can be powerful tools for initial screening of potential hazardous waste repository sites and can be used as part of larger matrix of self-consistent data providing insight into the appropriateness of a repository site. For instance, strong salinity gradients and high salinities at depth may indicate density stratification and imply a lack of mixing and/or upward movement of deep waters into shallower environments. Similarly, a low thermal flux through the geologic formation and/or low temperature gradients may suggest a limited or lack of thermally derived buoyant flow upward through a formation. In other instances, changes in the stable isotopic composition of the brines, for example shifts in the deuterium and 18-oxygen isotopic ratios away from the Global Mean Water Line, may indicate long term abiogenic water rock interactions in isolation from surface waters. Similarly, stratification of different life forms in the shallow vs. deep geo-biosphere with different metabolic requirements and isotopic markers may indicate that the different life forms exist in isolation from one another at different depths without mixing and transfer of nutrients from surface waters.

One or more of the above indirect markers (and others) may provide confirmation of: (a) the current lack of physical driving forces (e.g., saline-density and thermal buoyancy) to cause upward flow and mixing of the brines with shallow or surface waters; and/or (b) evidence that in the past, isolation of the deep brines from surface waters persisted for significant amounts of time as reflected in stable isotopic markers for water rock interaction and existence of distinct depth stratified microbial populations. These types of indirect markers may provide general indications of isolation but may not place strict time limits on the duration that deep brines have been isolated from the surface. At a minimum, these markers may indicate isolation of some thousands to tens of thousands of years, but may also be consistent with isolation of the deep brines from the surface environments for millions to >one billion years. As such, these example indirect markers may provide a secondary but important and independent system of corroborating geochronologic evidence that places explicit time limits for the isolation of brines at depth.

As an example, there may be direct geochronologic indicators of long-term (e.g., hundreds, to thousands, to tens of thousands, to millions of years) isolation of a fluid (e.g., brine liquid) in a particular subterranean formation. In order to place explicit time limits on the past isolation of deep brines, a number of geochronologic tools based on the production and decay of different stable and unstable isotopes in the Earth's atmosphere, surface, shallow subsurface (tens of meters), and deep subsurface (hundreds to thousands of meters) can be brought to bear. These geochronologic tools may have independent and distinct modes of production and together provide an integrated and internally self-consistent picture of: (a) the downward flow and mixing of surface waters with deep brines by tracing atmospheric and shallow subsurface derived cosmogenic radioisotopes (e.g., 81Kr, 36Cl, others) with a time frame of, e.g., 1-1.5 million years (Ma); (b) the medium term stagnancy and isolation of deep brines with a time frame of, e.g., 100 kiloyears (kyr)-80 Ma, through the measured concentration of nucleogenic isotopes produced in the deep subsurface (e.g., >100 m) that develop distinct secular equilibrium concentrations over long periods of time (36Clse 1-1.5 Ma, 129Ise 60-80 Ma, others); (c) the medium to very long term isolation of brines, e.g., 1 Ma>1 billion years (Ga), from the measured accumulation of different noble gas isotopes (4He, 40Ar, 20-21-22Ne, Kr, 124-139 Xe, and others), each of which has distinct modes of production in the deep subsurface and provides an independent measure of the retentiveness and isolation of deep brines.

As an example, each of the above mentioned geochronologic markers may provide an independent assessment of the isolation of deep brines within a subterranean formation and an independent measure of the suitability of the formation for use as a hazardous waste repository (e.g., for radioactive or nuclear waste). Used in combination, such geochronologic markers can provide a more compelling and complete picture of the mobility/stagnancy of brines in the sub surface.

For instance, in an example, a measurement of 81Kr, 36Cl, 20-21-22Ne isotopic abundances may be made from a sample of subterranean fluid (e.g., liquid brine) from a formation. The measurement may indicate that: (1) 81Kr is at or below detection limits of approximately 400 atoms/liter, (2) 36Cl concentrations are relatively high but 36Cl/Cl ratios are consistent with calculated secular equilibrium concentration values for the formation, and/or (3) there is a significant excess of 21Ne and a 21Ne/22Ne ratio of approximately 0.5. In such a case, the absence of 81Kr may be an indicator that there is either insignificant or no downward penetration of surface waters into the deep brine or very slow exchange and replacement of deep waters by surface waters (e.g., less than 1% exchange per 10,000 yrs.). The relatively high absolute concentration of 36Cl coupled with a low 36Cl/Cl ratio consistent with calculated 36Cl production in the deep subsurface may indicate that the brine has been stagnant and isolated from the surface for a minimum of 1-1.5 Ma. The accumulation and retention of 21Ne in the formation and 21Ne/22Ne ratio may indicate that the neon has been produced and retained in the deep formation for >100 Ma. Each of these isotopic systems represents a different and unique marker, e.g., of mode of production, and of estimate of isolation. That all three indicators agree may also provide cross checking of the markers and contributes to the overall certainty of the result.

In some aspects of the present disclosure, indirect markers of isolation may be used as proxies for direct markers. For example, in addition to the direct geochronologic measures, indirect markers of the isolation age of the brines such as (1) salinity-density stratification with depth, (2) distinct changes in stable isotopic measures such as oxygen and deuterium with depth, as well as (3) changes in the type, metabolic processes, and diversity of life forms as a function of depth, among other indicators, may serve as secondary supporting evidence and proxies for the long term isolation of deep brines. In some aspects, measuring these physical and chemical properties may be simpler, faster, and less expensive than performing detailed geochronologic age determinations. In some example aspects, simply collecting data on salinity, temperature and other proxies such as oxygen and deuterium isotopes can provide a good initial screening for a hazardous material repository site.

For example, if a potential hazardous waste repository site has relatively high heat flow and low salinity gradients as a function of depth, this may be an indication that the site has significant upwelling potential and relatively low probability of being appropriate for a nuclear waste repository. In contrast, if a site has relatively low thermal gradient and relatively steep increases in salinity at increasing depths this may correlate with stagnancy and isolation of brines at depth. If oxygen and deuterium (or other) isotopes further correlate with salinity, this may provide another indication that the brines at depth are density stratified and have been isolated over long time periods. This type of screening allows a number of sites (e.g., for a hazardous waste repository) to be initially evaluated in a relatively rapid manner and limit costs associated with difficult drilling, sampling and measuring processes associated with data on a broader suite of isotopes (e.g., 81-Kr, noble gases, and other isotopes). This initial screening may leverage the use of indirect proxies of isolation as a tool for locating and concentrating efforts on the most feasible sites, while saving costs and time associated with full detailed geochemical and isotopic measurements.

In some aspects, such implementations can be applied in subterranean formations that have natural uranium or thorium (or both) in the subterranean formation. Many sedimentary, metamorphic, and igneous rocks, including shale formations and crystalline basement rock, have suitable levels of uranium or thorium (or both) for the described implementations.

Figure 3A:
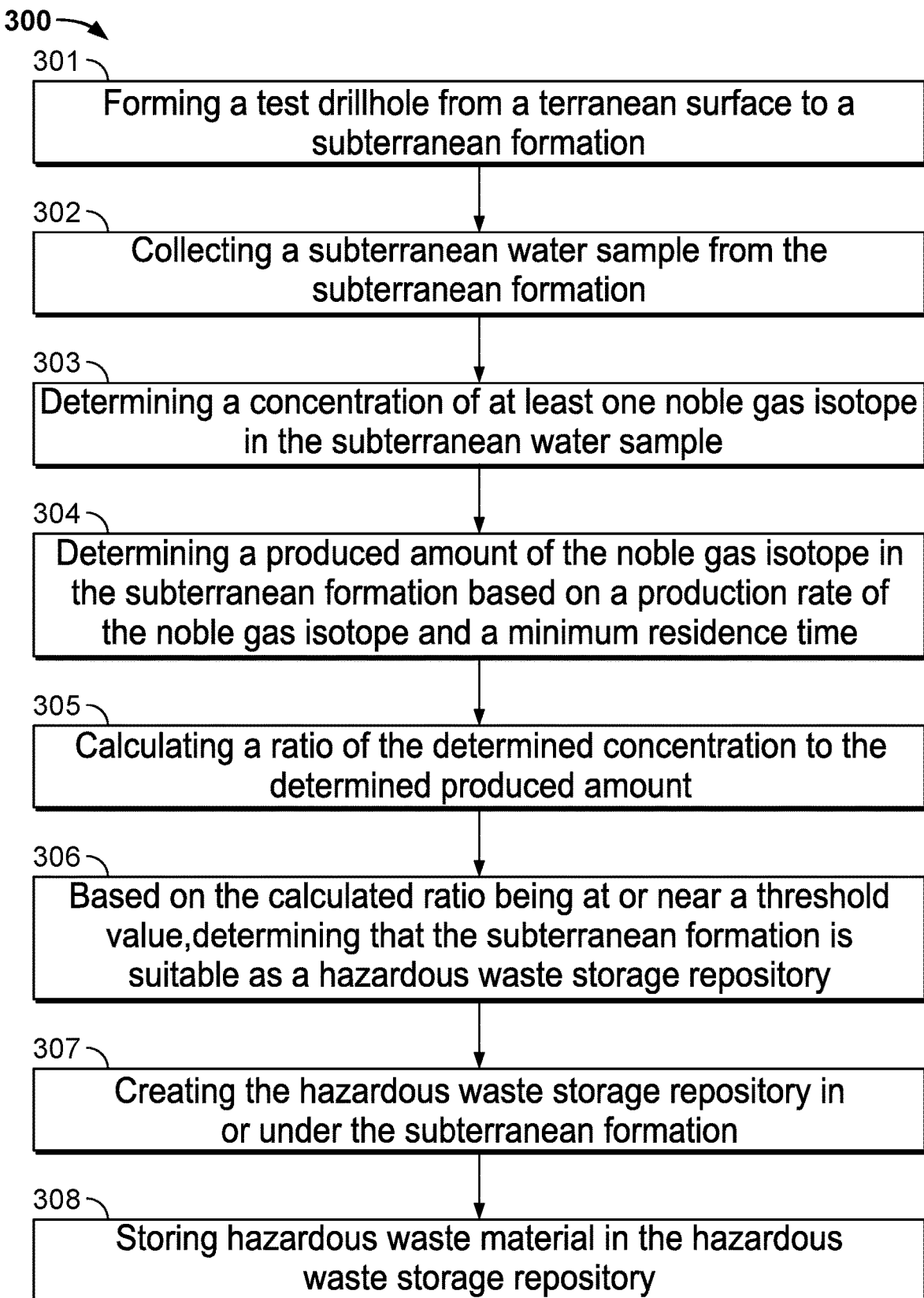
FIGS. 3A-3F are flowcharts that illustrate example processes for testing subterranean water to determine suitability of a subterranean formation as a hazardous waste repository according to the present disclosure.
Figure 3B:
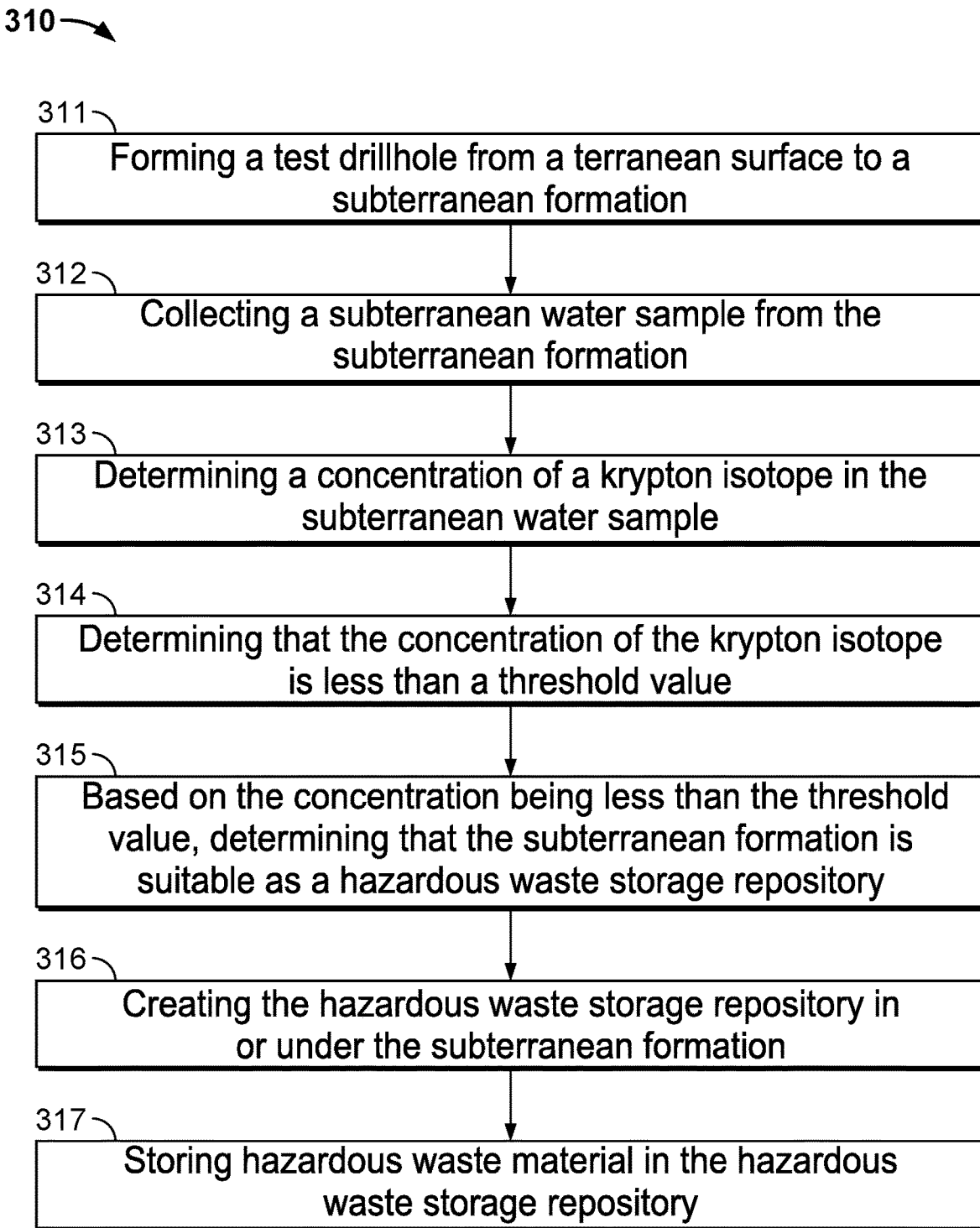

Turning now to FIG. 3A, this figure illustrates an example process 300 for determining the suitability of a subterranean formation as a hazardous waste repository by an analysis of a production and accumulation of one or more noble gas isotopes (and possibly other nuclides) in a subterranean formation based on a natural decay of one or more of uranium, thorium, or potassium (and possibly other secondary nucleogenic reactions). In some aspects, process 300 may be implemented by or with the system 100, including the fluid testing system 122.

Process 300 may be based on natural radioactive decay that occurs in deep subterranean formations and leads to the production of a variety of isotopes that were not present, or present in a lesser degree, in the original rock of the subterranean formation. For example, the alpha decay of uranium and thorium produces an alpha particle that consists of two neutrons and two protons. Additional alpha particles are produced from the radioactive decay of the uranium and thorium decay products. When one atom of U-238 decays, there are seven additional alpha particles produced from the decay products. Most of these alpha particles come to rest in the rock of the subterranean formation. Because of their strong positive charge, these alpha particles take the outer electrons from other atoms. The alpha+electrons are helium atoms, and these can accumulate in the rock. In many porous rocks, this produced helium diffuses away, and is often captured under "cap" formations that consist of impermeable rock. Such accumulations can be harvested, and they provide essentially all of commercial helium.

If, however, the rock has very low permeability, then the helium can be trapped in the rock. A measure of helium concentration, compared with the expected helium production from the uranium and thorium, may provide a measure of the retentiveness of the rock against gas diffusion or transportation by moving fluids. If, for example, the rock contains enough helium that it would have taken 10 million years to produce it from the uranium and thorium, then the ability of the subterranean formation to retain helium gas is approximately 10 million years. Such a determination can provide for a determination that the subterranean formation is suitable as a hazardous waste repository (e.g., formed in a deep, directional drillhole), since diffusion of one or more radioactive isotopes in nuclear or radioactive waste is known to be slower than that of helium.

Process 300 may begin at step 301, which includes forming a test drillhole from a terranean surface to a subterranean formation. For example, test drillhole 104 may be formed (e.g., drilled) from the terranean surface 102 to the subterranean formation 110. Process 300 may continue at step 302, which includes collecting a subterranean water sample from the subterranean formation. In some aspects, the water sample is brine. Alternatively, step 302 could include collecting a subterranean fluid sample. In some aspects, steps 301 and 302 may be replaced or avoided by identifying a previously collected subterranean fluid sample (e.g., liquid brine).

Process 300 may continue at step 303, which includes determining a concentration of at least one noble gas isotope in the subterranean water sample. For example, in the example of helium, a helium concentration may be determined from a liquid (e.g., brine) sample taken from the subterranean formation. For instance, helium is a dissolved gas in the brine, and standard downhole tools may be used to obtain a brine sample from the subterranean formation. If, however, the subterranean formation has very low brine flow rates (e.g., due to the pressure of the subterranean formation), a rock core sample that includes brine may be collected. Once the brine sample is collected (either directly or from a core sample), gas extraction methods may be used to collect the helium within the brine sample. In some aspects, the concentration of helium may depend on the rock type within the subterranean formation.

Process 300 may continue at step 304, which includes determining a produced amount of the noble gas isotope in the subterranean formation based on a production rate of the noble gas isotope and a minimum residence time. For instance, continuing the example of helium, once the concentration is determined (e.g., by known sampling techniques) from the brine sample, a production amount of the helium in the subterranean formation during an assumed or desired residence time (in atoms) is determined. Although a production rate (atoms per year) of helium in a subterranean formation may vary with geology, this rate is a function of the concentrations of uranium and thorium in the formation (i.e., an amount of uranium and thorium per unit volume of formation). In some aspects, the concentration of uranium and/or thorium, and thus the production rate of helium (or another noble gas isotope), may be known or determined by the known bulk rock chemistry of the subterranean formation. In some aspects, the residence time represents a time period in which the helium was fluidly isolated in the subterranean formation, as well as a time period in which it is desired for hazardous waste to be stored and fluidly isolated within the subterranean formation, e.g., thousands of years, tens of thousands of years, millions or years, or other time period.

Process 300 may continue at step 305, which includes calculating a ratio of the determined concentration to the determined produced amount of the at least one noble gas isotope. For example, continuing with the helium example, the determined concentration represents an actual amount (e.g., concentration) of helium in the subterranean formation being examined as a potential hazardous material repository. The determined produced amount represents, e.g., the theoretical amount (e.g., concentration) of helium that should be present in the subterranean formation at a particular minimum residence time of the fluid sample from the formation. The particular minimum residence time, as described, may be selected, e.g., based on a desired amount of time for which hazardous waste stored in the subterranean formation is isolated (e.g., from a source of mobile water) within the subterranean formation. This time period could be, for example, tens of years, hundreds of years, thousands of years, or more (or, in some cases, less).

Process 300 may continue at step 306, which includes determining that the subterranean formation is suitable as a hazardous waste storage repository based, at least in part, on the calculated ratio being at or near a threshold value. In some aspects, the threshold value may be 1 or very close to 1, thereby showing that the helium concentration in the subterranean fluid sample has been isolated within the formation for at or near the desired minimum residence time duration. For example, if the calculated ratio is much less than 1, the determined concentration is much less than the determined produced amount, thereby showing that helium has escaped the subterranean formation (i.e., has not been fluidly isolated from other formations, including possibly, formations with mobile or surface water). If the calculated ratio is greater than 1, the determined concentration is greater than the determined produced amount, thereby showing that helium has not escaped the subterranean formation (i.e., has been fluidly isolated from other formations, including possibly, formations with mobile or surface water).

Process 300 may continue at step 307, which includes creating the hazardous waste storage repository (or at least initiating creation of the hazardous waste repository) in or under the subterranean formation based on the determination of step 306. Process 300 may continue at step 308, which includes storing hazardous waste material in the hazardous waste storage repository. Example methods and processes for steps 307 and 308 are described with reference to FIGS. 2A-2B and 4.

In some aspects, process 300 includes repeating steps 303-305 but for a different noble gas isotope than a noble gas isotope original tested in the subterranean fluid sample. For example, as described, helium is a particular noble gas isotope with a particular production mode. The fluid sample may also be tested for a different noble gas isotope than helium, which may have a different production mode than helium. In some aspects, another ratio of a determined concentration to a determined produced amount of the other noble gas isotope is calculated and compared against the threshold value. If the other calculated ratio is at or near the threshold value, this determination may be further confirmation that the subterranean formation is suitable as a hazardous waste storage repository. The additional calculated ratio of the determined concentration to the determined produced amount of the other noble gas isotope can also be compared to the first calculated ratio. This comparison (e.g., if the calculated ratios are equal or close to equal) may also be further confirmation that the subterranean formation is suitable as a hazardous waste storage repository.

As described, different noble gas isotopes may have different production modes; an example production mode for helium was previously described. In alternative aspects, when alpha particles from uranium or thorium decay are emitted, instead of stopping and becoming the core of helium atoms, they frequently collide with the nuclei of other elements (e.g., aluminum, silicon, magnesium, oxygen and fluorine), and in rare instances (less than 1:10 million) result in the capture of alpha particle by the element. The capture of alpha particles can result in the production of other rare noble gas isotopes which can also be used to determine the length of time these rare isotopes have been accumulating in the subsurface.

As an illustrative example, consider the noble gas isotope of neon, which has three stable isotopes: neon-20 (Ne-20), neon-21 (Ne-21), and neon-22 (Ne-22). The natural concentrations of these isotopes are 90.48%, 0.27%, and 9.25%, respectively. However, when neon is exposed to subsurface alpha radiation over millions of years, the absorption of the alpha particles (primarily by oxygen, fluorine and magnesium isotopes) drastically changes both the absolute concentrations of the isotopes and their ratios relative to one another. The rate of production of the different neon isotopes depends on the concentration of the target isotopes (17O, 18O, 19F in this instance) within a ~40 micron radius of the U or Th emitter. The principal nuclear reactions are 17O($\alpha$,n)Ne-20, 18O($\alpha$,n)Ne-21, and 19F($\alpha$,n)Ne-22. Production of neon isotopes through ($\alpha$,n) reactions in the subsurface dramatically favor the production of Ne-21 relative to its original isotopic abundance. As a result, over long time periods the absolute and relative abundances of Ne-21 change. In deep subterranean formations, the Ne-21/Ne-22 ratio has been observed to grow from 0.027 to 0.6, a 20 fold increase. Such dramatic changes in isotopic composition provide evidence for tens to hundreds of millions of years of an accumulation of Ne-21. Since the excess was produced after the rock in the subterranean formation was formed, the presence of this excess of Ne-21 is a measure of the retention capability of the subterranean formation for the gas, neon.

Additional changes in the concentration of other noble gases, e.g., argon, krypton and xenon, produced by a number of subsurface nucleogenic reactions (beta decay of 40K to 40Ar, fission of 238U for the production of Xe isotopes, and other reactions) also contribute information on the isolation and stagnancy of the brines. Thus, the measurement of ratios of the isotopes of the noble gases helium, argon, neon, krypton, and xenon offer an estimation of the fluid isolative capabilities of the subterranean formation. Thus, in some aspects, such an estimation may provide a determination that the subterranean formation is suitable as a hazardous waste repository for, e.g., radioactive waste. Because each of these noble gas isotopic systems has a different mode of production, each provides an independent estimate of the fluid isolative capacity of deep brines. The use of multiple noble gas isotopes as independent geochronologic markers to estimate the age and isolation of brine in deep geologic formations provides a powerful and integrated system of cross checking and validating the age and isolation estimates.

The present disclosure also describes a process for determining the suitability of a subterranean formation as a hazardous waste repository based on a measurement of a krypton isotope from a fluid sample from the subterranean formation. For example, turning to FIG. 3B, this figure illustrates an example process 310 for determining the suitability of a subterranean formation as a hazardous waste repository based on a measurement of a krypton isotope from a fluid sample from the subterranean formation. In some aspects, process 310 may be implemented by or with the system 100, including the fluid testing system 122.

For example, in example implementations, a measurement of an amount of krypton-81 (Kr-81) in a subterranean formation (e.g., within a liquid such as brine in the formation) may be used to determine the suitability of the subterranean formation as a hazardous waste repository. For example, in deep subterranean formations, another measure of a fluid isolative capability of the formation may include a determination that surface water (e.g., from a body of water on a terranean surface or a shallow aquifer) are not appreciably mixing with brine in the subterranean formation. One measure of this isolation is the absence of radionuclides produced in the earth's atmosphere or near subsurface at depth. One example radioisotope to demonstrate this isolation is the specific noble gas krypton-81 (half-life 229,000 years), which is produced at the Earth's surface, is incorporated and travels with surface waters, and has no significant subsurface production mode. If surface waters are mixing significantly with brine in the subterranean formation, Kr-81 would be present in the brine in measurable quantities. If no Kr-81 is observed within the brine in the subterranean formation, then the age limit will be determined by the precision with which that zero level is determined. This age limit may be about 1.5 million years.

Thus, the absence of measurable Kr-81 in a subterranean formation at current measurement sensitivities indicates that the brine in that subterranean formation has been fluidly isolated from the terranean surface or shallow aquifers for 1.5 million years or more. Thus, measurement of Kr-81 in a subterranean formation may offer an estimation of the fluid isolative capabilities of the subterranean formation. Thus, in some aspects, such an estimation may provide a determination that the subterranean formation is suitable as a hazardous waste repository for, e.g., radioactive waste.

Process 310 may begin at step 311, which includes forming a test drillhole from a terranean surface to a subterranean formation. For example, test drillhole 104 may be formed (e.g., drilled) from the terranean surface 102 to the subterranean formation 110. Process 310 may continue at step 312, which includes collecting a subterranean water sample from the subterranean formation. In some aspects, the water sample is brine. Alternatively, step 312 could include collecting a subterranean fluid sample. In some aspects, steps 311 and 312 may be replaced or avoided by identifying a previously collected subterranean fluid sample (e.g., liquid brine).

Process 310 may continue at step 313, which includes determining a concentration of a krypton isotope in the subterranean water sample. For example, in some aspects, a concentration of Kr-81 may be determined from the water (or fluid) sample. In some aspects, as Kr-81 may be very scarce, the water sample may be on the order of 10-100 liters. The Kr-81 concentration may be measured using Atom Trap Trace Analysis (ATTA), a system that traps individual atoms of Kr-81 in the fluid sample and counts these atoms.

Process 310 may continue at step 314, which includes determining that the concentration of the krypton isotope is less than a threshold value. For example, once the concentration of the Kr-81 in the subterranean fluid sample is determined, it may be compared to a known concentration of Kr-81 in surface water samples (e.g., a threshold value). For example, in a surface water sample, an average Kr-81 concentration may be about 1300 atoms/liter. After about 4-5 half-lives (and accounting for an 80% extraction efficiency), there may be about 60 atoms to remain per liter.

Process 310 may continue at step 315, which includes determining that the subterranean formation is suitable as a hazardous waste storage repository based, at least in part, on the concentration being less that the threshold value. For example, in order to determine if the subterranean fluid sample concentration is low enough to show that the subterranean formation has suitable fluid isolative capabilities (i.e., that the Kr-81 has been isolated in the subterranean formation away from a mobile water or surface water formation). ATTA may use 100 liter samples, so in the example case in which the subterranean formation is suitable for a hazardous waste repository, there would be about 6000 atoms of Kr-81 remaining. Counting efficiency in ATTA is about 1-2%; thus, of the 6000 atoms remaining, the ATTA would count about 60-120 atoms from the brine sample. Such a concentration of Kr-81 in the brine sample from the subterranean formation (i.e., 60-120 count) effectively shows that the subterranean formation is suitable as a hazardous waste repository in accordance with the Kr-81 analysis described herein.

Process 310 may continue at step 316, which includes creating the hazardous waste storage repository (or at least initiating creation of the hazardous waste repository) in or under the subterranean formation based on the determination of step 315. Process 310 may continue at step 317, which includes storing hazardous waste material in the hazardous waste storage repository. Example methods and processes for steps 316 and 317 are described with reference to FIGS. 2A-2B and 4.

The present disclosure also describes analyses of additional isotopes that are formed through subsurface nuclear processes such as Cl-36, I-129, and Ar-39 and can provide still other independent and complementary means of assessing the age and isolation of brines. For example, when alpha particles from uranium or thorium decay are emitted, instead of stopping and becoming the core of helium atoms, they frequently collide with the nuclei of other elements (e.g., aluminum, silicon, magnesium, oxygen and fluorine), and cause the release of neutrons from these target elements. Measurements of the uranium and thorium concentrations, combined with estimates or measurements of bulk rock chemistry, allow for the estimation of a neutron flux within the subterranean formation. A produced neutron could come to rest and decay (with a half-life of 10.3 minutes), but more typically, the produced neutron is absorbed on another nucleus in the formation. The result of the absorption is a new isotope.

When neutrons are absorbed on some stable nuclei, they can create unstable, that is, radioactive elements. For example, a neutron absorbed on the nucleus of chlorine-35 (Cl-35) (the most abundant stable isotope of chlorine) forms chlorine-36 (Cl-36), a radioactive atom with a half-life of 301,000 years. If none of the chlorine is carried away, or diffuses away through the rock in the formation, then the concentration of Cl-36 will continue to accumulate until the production rate (fixed by the neutron flux and Cl-35 concentrations) matches the decay rate (which increases proportional to the amount of Cl-36 presents). This isotopic equilibrium ratio is reached asymptotically, but most of it is accomplished after 4 to 5 half-lives of Cl-36, that is, after 1.2-1.5 million years.

This isotopic equilibrium ratio of Cl-35 and Cl-36 can be calculated from the abundances of Cl-35, uranium and thorium, and from the chemical composition of the rock in the subterranean formation. However, this isotopic equilibrium ratio will not be reached if the chlorine is escaping from the subterranean formation (e.g., in liquid that is mobile and, for instance, moves toward the terranean surface). In that case, a lower value for the ratio will indicate that the residence time of the chlorine atom in the formation is less than 1.5 million years. In some aspects, such a ratio may be informative for the determination of whether or not the subterranean formation is suitable as a hazardous waste repository, since Cl-36, itself, is a threat to human health from leakage of underground waste. Thus, measurement of ratios of the isotopes of chlorine offer an estimation of the fluid isolative capabilities of the subterranean formation. Thus, in some aspects, such an estimation may provide a determination that the subterranean formation is suitable as a hazardous waste repository for, e.g., radioactive waste.

Other isotopes can also be used in a similar fashion. One of these is iodine-129 (I-129), which has a half-life of 16 million years. This isotope is produced underground by fissions of uranium and thorium. I-129 reaches a steady state level in 4-5 half lives, or 60-70 million years. Deviation from this steady-state level may show that the iodine is diffusing or being carried away on a time-scale of several million years or less. Thus, measurement of ratios of the isotopes of iodine offer an estimation of the fluid isolative capabilities of the subterranean formation. Thus, in some aspects, such an estimation may provide a determination that the subterranean formation is suitable as a hazardous waste repository for, e.g., radioactive waste.

According to example embodiments, determination of isotopic equilibrium ratios as described herein (e.g., with respect to noble gases, chlorine, iodine as examples) may include accurately calculating neutron flux (e.g., by the fluid testing system 122). For example, neutron flux can be determined by determining a gamma ray flux (for example, by downhole gamma ray logging instruments). The determined gamma ray flux can then be used to estimate a uranium or thorium decay rate (or both). From the calculated decay rate (or rates), an alpha-particle flux can be determined. From one or more rock samples collected from the subterranean formation, measurements of an abundance of the alpha targets that create the most neutrons (e.g., one or more of aluminum, silicon, magnesium, or oxygen) are taken. From these measurements, the neutron flux can be calculated with sufficient precision to allow the isotopic equilibrium ratio determination to be used to then estimate the fluid isolative capability of the subterranean formation.

In some aspect, a high precision of the neutron flux determination is useful. Direct measurement of neutron fluxes in the subterranean formation using neutron monitors could reduce uncertainties. In some aspects, the neutron flux may be too low for such a system to be practical and typically requires months of observation.

In some aspects of the present disclosure, accurate neutron flux may be determined by determining a concentration of a nucleonic isotope produced in the subterranean formation that is also radioactive and has a short enough half-life that the isotope will reliably be in a state of isotopic equilibrium when measured. For instance, since such a measurement determines neutron flux due to the short time in which equilibrium is reached, there may be very little loss to flow.

In an example implementation, the isotope is argon-39 (Ar-39). Argon-39 is produced from neutron capture reaction, $^{39}K(n,p)^{39}Ar$, and has a half-life of 269 years. Potassium-39 (K-39) is the most abundant potassium isotope (93%) and is among the most common constituents of rock forming minerals. Potassium-39 concentrations, coupled with measurements of Ar-39 and with a known neutron capture cross section of K-39, provide a direct measure of the subsurface neutron flux, averaged over approximately 1500 years, the time needed to reach the isotopic equilibrium concentration of argon-40 (Ar-40). This neutron flux estimate established by direct measurement can then be applied to calculations for production rate of longer-lived radionuclides (e.g., Cl-36) and of other nucleogenic stable isotopes. This method offers a considerable improvement over both first principle estimates of neutron fluxes and inferred neutron flux estimates based on gamma rays.

In some aspects, the neutron flux is an intermediate parameter in the determination according to the described implementations. Thus, in effect, it is the measurement of the ratio of Ar-39 to other isotopes that determines the presence of isotopic equilibrium and thus of suitability of the formation for use as a hazardous waste repository.

The present disclosure also describes a process for determining the suitability of a subterranean formation as a hazardous waste repository based on a measured neutron flux of one or more isotopes. For example, turning to FIG. 3C, this figure illustrates an example process 320 for determining the suitability of a subterranean formation as a hazardous waste repository based on a calculated neutron flux of a particular isotope and a predicted production rate of a second isotope that is based on the calculated neutron flux. The predicted production rate is compared against a concentration of the second isotope found in a subterranean fluid sample. In some aspects, process 320 may be implemented by or with the system 100, including the fluid testing system 122.

Process 320 may begin at step 321, which includes forming a test drillhole from a terranean surface to a subterranean formation. For example, test drillhole 104 may be formed (e.g., drilled) from the terranean surface 102 to the subterranean formation 110. Process 320 may continue at step 322, which includes collecting a subterranean water sample from the subterranean formation. In some aspects, the water sample is brine. Alternatively, step 322 could include collecting a subterranean fluid sample. In some aspects, steps 321 and 322 may be replaced or avoided by identifying a previously collected subterranean fluid sample (e.g., liquid brine).

Process 320 may continue at step 323, which includes determining a neutron flux of a first isotope in the subterranean formation. In some aspects, the first isotope may be one of Ar-39, Fe-59, Co-60, Ni-63, Kr-85, Ni-63, or C-14. In some aspects, the neutron flux may be determined according to the bulk rock chemistry of the subterranean formation (e.g., an amount of uranium or thorium (or both) per unit volume of the subterranean formation). In some aspects, a neutron flux value may be determined for a (relatively) short-lived radioisotope, such as Ar-39, which is produced from K-39 through neutron capture from the release of alpha particles from uranium or thorium decay (or both). Thus, the bulk rock chemistry of the subterranean formation, which indicates an amount of uranium or thorium in the subterranean formation, indicates an amount of neutrons that are released to produce Ar-39 from K-39. From this information, the neutron flux value for Ar-39 can be determined.

Process 320 may continue at step 324, which includes calculating, based at least in part on the determined neutron flux, a predicted production rate of a second isotope in the subterranean formation. In some aspects, the second isotope is Cl-36. A stable form of Cl-36 is Cl-35. In any event, in some aspects, the first isotope has a shorter half-life (e.g., in years) than the second isotope. For instance, once the neutron flux for, e.g., Ar-39, is determined, this value can be used to determine a predicted production rate of other, longer lived, substances in the subterranean formation, such as, for example, radioisotopes like Cl-36.

Process 320 may continue at step 325, which includes calculating a first ratio of the predicted production rate of the second isotope relative to a theoretical production rate of a stable form of the second isotope. In some aspects, a ratio of the predicted production rate of, e.g., Cl-36, with the predicted production of the respective stable (or other) isotope, e.g., Cl-35 (or Cl). The predicted production rate, in this example, of the stable isotope is based on the bulk rock chemistry of the subterranean formation and assumes no migration of the stable isotope out of the subterranean formation (i.e., assumes the subterranean formation is fluidly isolative of the stable isotope).

Process 320 may continue at step 326, which includes measuring respective concentrations of the second isotope and the stable form of the second isotope in the subterranean water sample. For example, the subterranean water (or fluid) sample from the subterranean formation of step 344 is measured to determine concentrations of the longer lived isotope and a stable form of the longer lived isotope. For example, concentrations of, e.g., Cl-36, as well as, e.g., Cl-35 (or Cl), respectively, are determined.

Process 320 may continue at step 327, which includes calculating a second ratio of the measured concentration of the second isotope relative to the measured concentration of the stable form of the second isotope. For example, a ratio of the measured concentration of, e.g., Cl-36 with the measured concentration of the respective stable (or other) isotope, e.g., Cl-35 (or Cl) is determined.

Process 320 may continue at step 328, which includes determining that the subterranean formation is suitable as a hazardous waste repository based at least in part on a comparison of the first and second ratios. For instance, as the first ratio represents a ratio that assumes that the subterranean formation isolates fluid therewithin from other formations for a sufficient period of time (e.g., tens, hundreds, thousands, or millions of years), if the comparison of step 356 is equal or within a sufficiently small deviation from equal, the subterranean formation may be determined to be suitable for a hazardous waste repository.

Process 320 may continue at step 329, which includes creating the hazardous waste storage repository (or at least initiating creation of the hazardous waste repository) in or under the subterranean formation based on the determination of step 328. Process 320 may continue at step 330, which includes storing hazardous waste material in the hazardous waste storage repository. Example methods and processes for steps 329 and 330 are described with reference to FIGS. 2A-2B and 4.

Figure 3C:
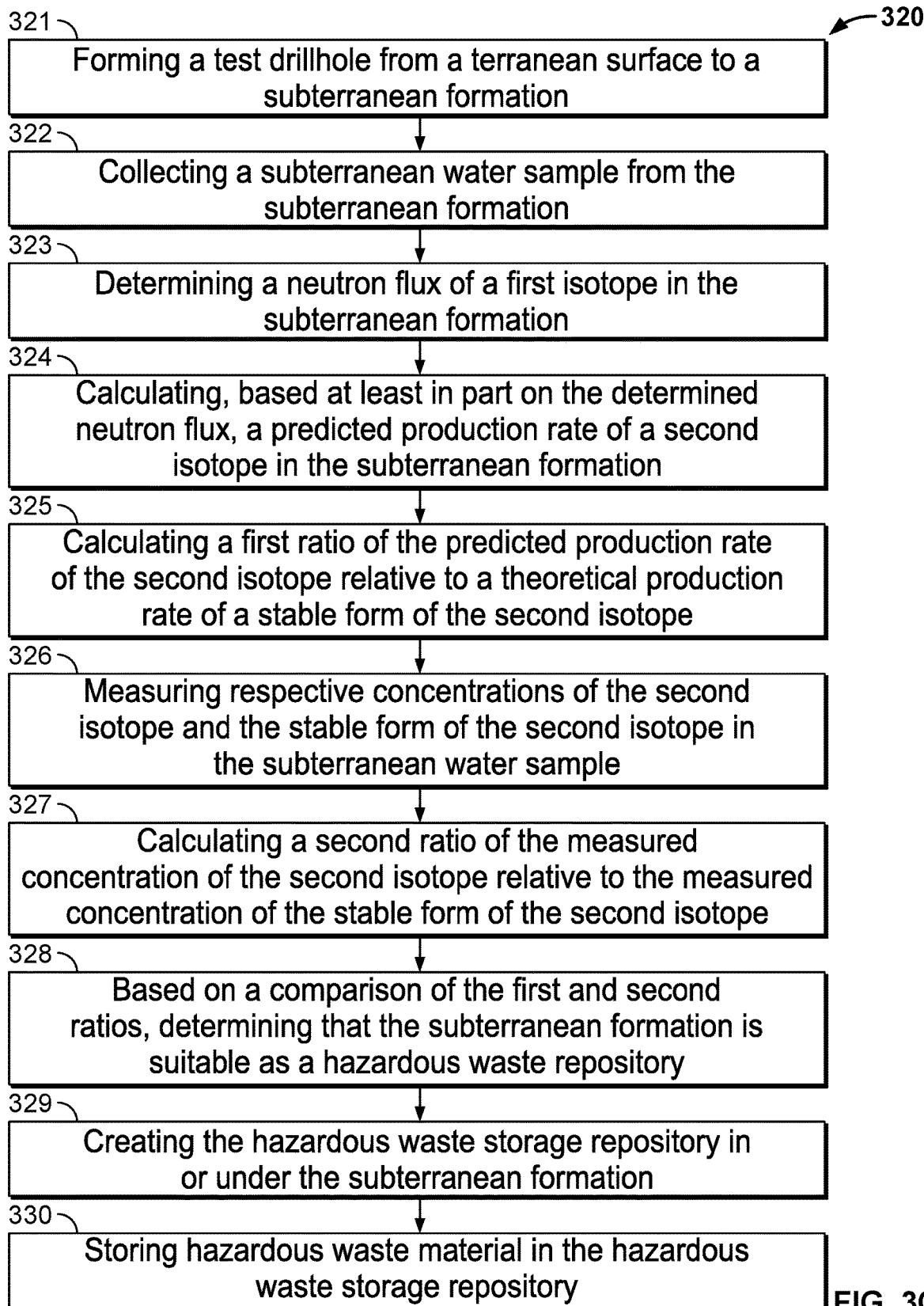

Thus, implementations of the present disclosure according to FIG. 3C use a short-lived radioisotope, which is created by local neutron fluxes but which exists for such a relatively short time that it is not depleted by flow or by diffusion, for the purpose of providing a calibration for the interpretation of longer-lived species, and for the determination of whether these long-lived species are in isotopic equilibrium. Other relatively short-lived isotopes could be used in place of Ar-39, such as Fe-59 (44.5 day half-life), Co-60 (5.3 year half-life), Ni-63 (100 year half-life), Kr-85 (half-life of 10.8 year half-life), nickel-63 (100 year half-life), carbon-14 (5730 year half-life), and others that are produced when neutron collide with elements in the rock of the subterranean formation.

Figure 3D:
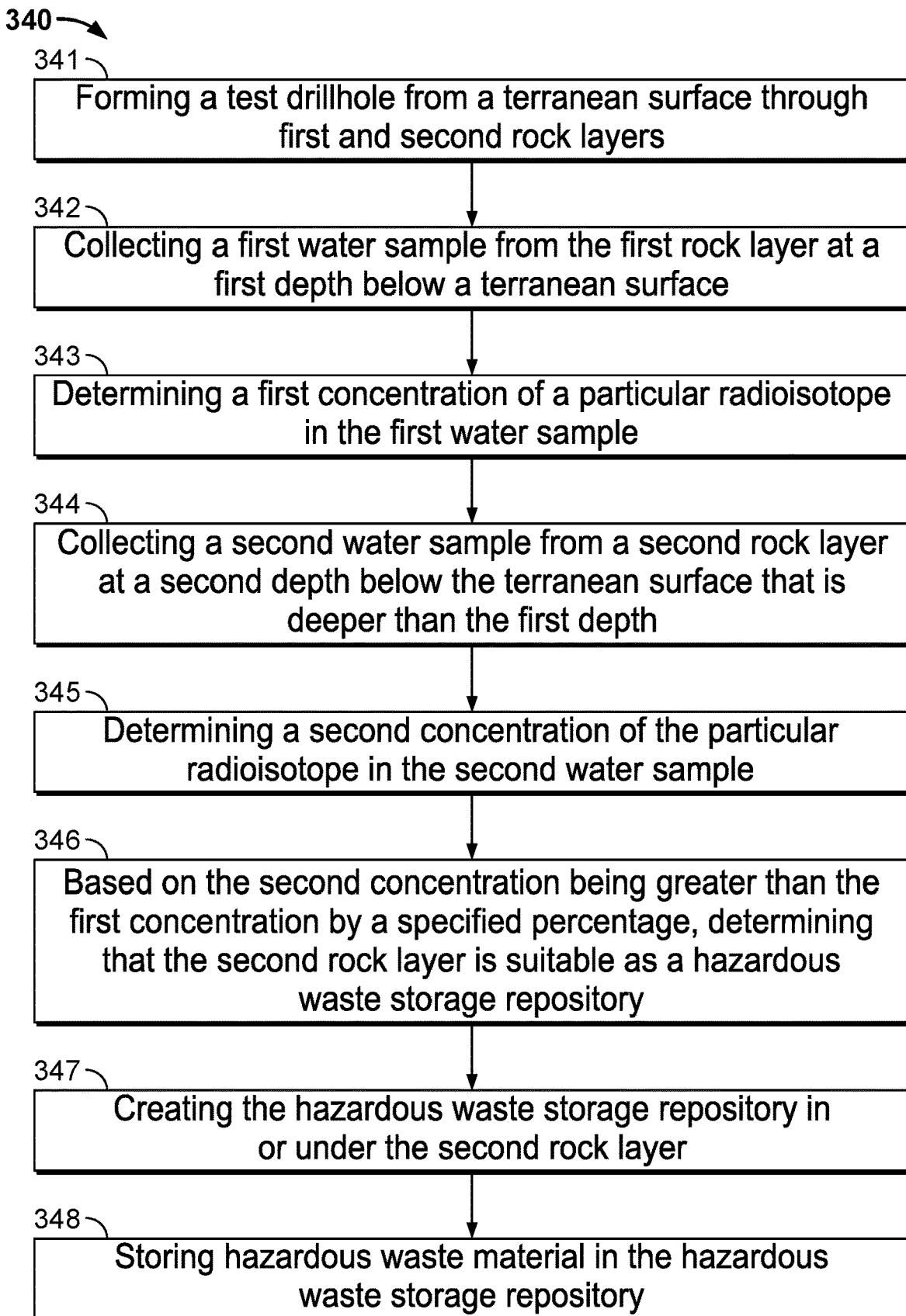

Turning now to FIG. 3D, this figure illustrates an example process 340 for determining the suitability of a subterranean formation as a hazardous waste repository by an analysis of concentrations of one or more radioisotopes entrained in subterranean fluid (e.g., brine) within subterranean formations located at different vertical depths below a terranean surface to show mobility (or lack thereof) of the subterranean fluid. In some aspects, process 340 may be implemented by or with the system 100, including the fluid testing system 122.

For example, process 340 may include measurements of concentrations of certain radioisotopes at depth that can be used as an indicator that water has not been transported to that depth from the terranean surface for thousands to millions of years. For instance, several radioisotopes are produced in the biosphere by cosmic rays. Such radioisotopes lower concentration or absence at depth indicates that their transport from the surface has taken many half-lives. Example radioisotopes for this approach include C-14, Cl-36, Kr-81, and I-129.

These examples, however, may give limits on the downward migration of radioisotopes, not on the upward migration. The two limits may be linked, but it is also advantageous to make a determination of water mobility in a subterranean zone that places limits on the upward migration of, e.g., radioisotopes.

Generally, process 340 describes an example implementation that includes measuring a concentration of one or more radionuclides per volume (e.g., liter) of water as a function of depth from a terranean surface and, based on the measurement(s) determining an upward water mobility in a subterranean zone. For example, radioisotopes deep in the earth come from several sources. Some examples include: (1) Radioisotopes produced in the biosphere that have migrated to depth; (2) Primordial radioisotopes, created in the formation of the solar system, and which are still present in geologic formations because of their long half-lives, and include, e.g., U-238, U-235, Th-232, and K-40; (3) Secondary radioisotopes produced deep in the Earth from the primordial radioisotopes, including I-131 (a fission fragment from uranium and thorium fission) and radioisotopes produced from neutron absorption, including Cl-36.

In some aspects of process 340, radioisotopes of either (1) or (2), or both, may be measured. Measurements on such radioisotopes can provide determinations and limits on upward radioisotope migration. This determination can then be used to determine the suitability of a subterranean zone from which the water sample was taken as a hazardous waste repository in which hazardous waste (e.g., nuclear waste such as spent nuclear fuel or high level waste) can be stored in deep, human-unoccupiable drillholes.

Process 340 may begin at step 341, which includes forming a test drillhole from a terranean surface through first and second rock layers (i.e., below a terranean surface). For example, test drillhole 104 may be formed (e.g., drilled) from the terranean surface 102 to and through subterranean formations 108 and 110. In some aspects, the first and second rock layers are located in adjacent (e.g., contacting) subterranean formations. In some aspects, the first and second rock layers may be separated by one or more intervening subterranean formations. In some aspects, the first and second rock layers may comprise a single rock type, but in distinct layers.

Process 340 may continue at step 342, which includes collecting a first water sample from the first rock layer at a first depth below the terranean surface. In some aspects, the water sample is brine. Alternatively, step 342 could include collecting a fluid sample. In some aspects, steps 341 and 342 may be replaced or avoided by identifying a previously collected water sample (e.g., liquid brine) from the first rock layer.

Process 340 may continue at step 343, which includes determining a first concentration of a particular radioisotope in the first water sample. In some aspects, the particular isotope may be uranium (U) and/or thorium (Th). In some aspects, the concentration can be determined using gamma ray logs, e.g., using downhole wellbore logging tools that measure natural gamma rays as a function of depth from the terranean surface. Such logs are typically interpreted as evidence of rock type, since some rocks (e.g., shale) typically have higher concentrations of these isotopes than do other rock types (e.g., limestone). Some of the gammas come from K-40 (high in clay) and others come from uranium and thorium. In some aspects, for the purpose of isolation determination, gamma ray logs may be used as an initial indicator of a degree of upward water mobility in a rock formation. Thus, step 343 may also include determining a concentration of U and/or Th from a core sample taken from the first rock layer.

As another example, the particular radioisotope may be potassium 40, abbreviated as K-40, which also serves as a tracer for elements that have similar transport properties to potassium. Step 343 may therefore include determining a concentration of K-40 in the first water sample.

As other examples, both Cl-36 and I-129 may be the particular radioisotope. These radioisotopes are produced underground due to the spontaneous fission of U-238. Thus, high levels of Cl-36 and I-129 are expected to be found in formations, such as shale, that are high in uranium. The iodine is typically a direct fission fragment, while the chlorine is produced when a neutron from the fission is absorbed onto the abundant and stable isotope, Cl-35. Step 343 may therefore include determining a concentration of Cl-36 and/or I-129 in the first water sample.

Process 340 may continue at step 344, which includes collecting a second water sample from the second rock layer at a second depth below the terranean surface that is deeper than the first depth. In some aspects, the water sample is brine. Alternatively, step 344 could include collecting a fluid sample. In some aspects, step 344 may be replaced or avoided by identifying a previously collected water sample (e.g., liquid brine) from the second rock layer.

Process 340 may continue at step 345, which includes determining a second concentration of the particular radioisotope in the second water sample. Step 345, in some aspects, may be similar to step 343, but with the second water sample rather than the first. Thus, subsequent to step 345, there are two concentrations determined of the particular radioisotope at two different depths under the terranean surface.

Process 340 may continue at step 346, which includes determining that the second rock layer is suitable as a hazardous waste storage repository based at least in part on the second concentration being greater than the first concentration by a specified percentage. In some aspects, the specified percentage may be, e.g., 50% or greater.

Process 340 may continue at step 347, which includes creating the hazardous waste storage repository (or at least initiating creation of the hazardous waste repository) in or under the second rock layer based on the determination of step 346. Process 340 may continue at step 348, which includes storing hazardous waste material in the hazardous waste storage repository. Example methods and processes for steps 347 and 348 are described with reference to FIGS. 2A-2B and 4.

As described, example implementations of process 340 indicate—by a showing that a particular radioisotope is more highly concentrated in a deeper rock layer relative to a shallower rock layer—that the deeper rock layer has fluidly isolated the particular radioisotope in the deeper rock layer for a desired time duration (e.g., tens, hundreds, thousands, or millions of years). Such a showing may indicate that the deeper rock layer is suitable as a hazardous waste repository.

For example, in the case of the radioisotope being K-40, the presence of a first rock layer having a high concentration of K-40 (measured in atoms per volume of water) with a second rock layer with a low concentration of K-40 above the first rock layer provides an indication that the K-40 in the first rock layer is not upwardly mobile. As another example, a presence of a deep layer with high uranium/thorium that is below a layer that is low in these elements may indicate little to no upward water (i.e., containing the U or Th) mobility in the deeper layer. For example, the presence of a low U/Th concentration layer above a layer with a high U/Th concentration gives an indication that uranium and thorium have not been migrating upward for periods of millions of years. Such a determination is useful for showing that uranium and thorium isotopes, if released from disposed fuel, would not migrate quickly to the surface. Besides uranium or thorium, other radioisotopes, which have similar chemistry to that of uranium and thorium, such as Americium, may also be measured as described above.

As another example, an estimation of upward water flow can be made by measuring the Cl-36 and I-129 levels in rock formations that lie above a formation in which hazardous waste is to be stored. Since the main mechanism for transport of these isotopes may be transport by moving water, the measurement should be made as concentrations (number of atoms) per volume of water in the selected formation(s). A concentration in a first rock layer that is substantially less than the concentration in a second, deeper rock level is an indicator that water transport from the second rock layer to the first layer takes more time than the half-lives of the measured radioisotopes. In some aspects, a flow of both Cl-36 and I-129 might be slower than a flow of the water that carries them, because chlorine and iodine can be absorbed for varying periods of time on the surrounding rock and later released. However, for the disposal of nuclear waste, the important number is not the velocity of flow of the water (which may be harmless) but the velocity of flow of the radioisotopes. In particular, the radioisotopes Cl-36 and I-129 are of concern since they are abundant in nuclear waste and long lived. For that reason, the measurement of upward flow of naturally occurring Cl-36 and I-129 is even more directly relevant to the suitability of a subterranean formation to safely (e.g., without upward leakage) store such nuclear waste (e.g., for hundreds if not thousands or millions of years) than is the actual flow of water (or other fluid).

Figure 3E:
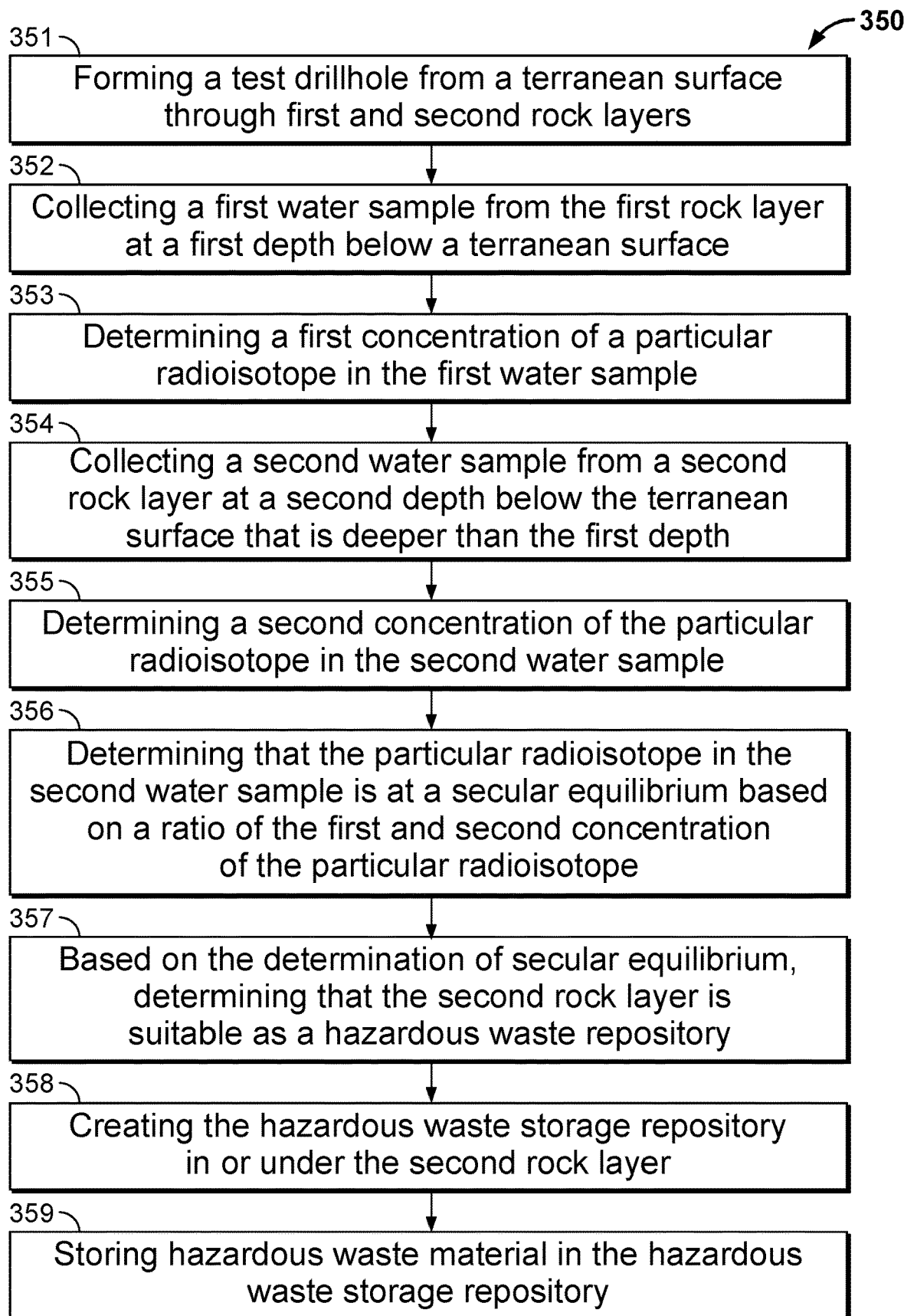
Figure 3F:
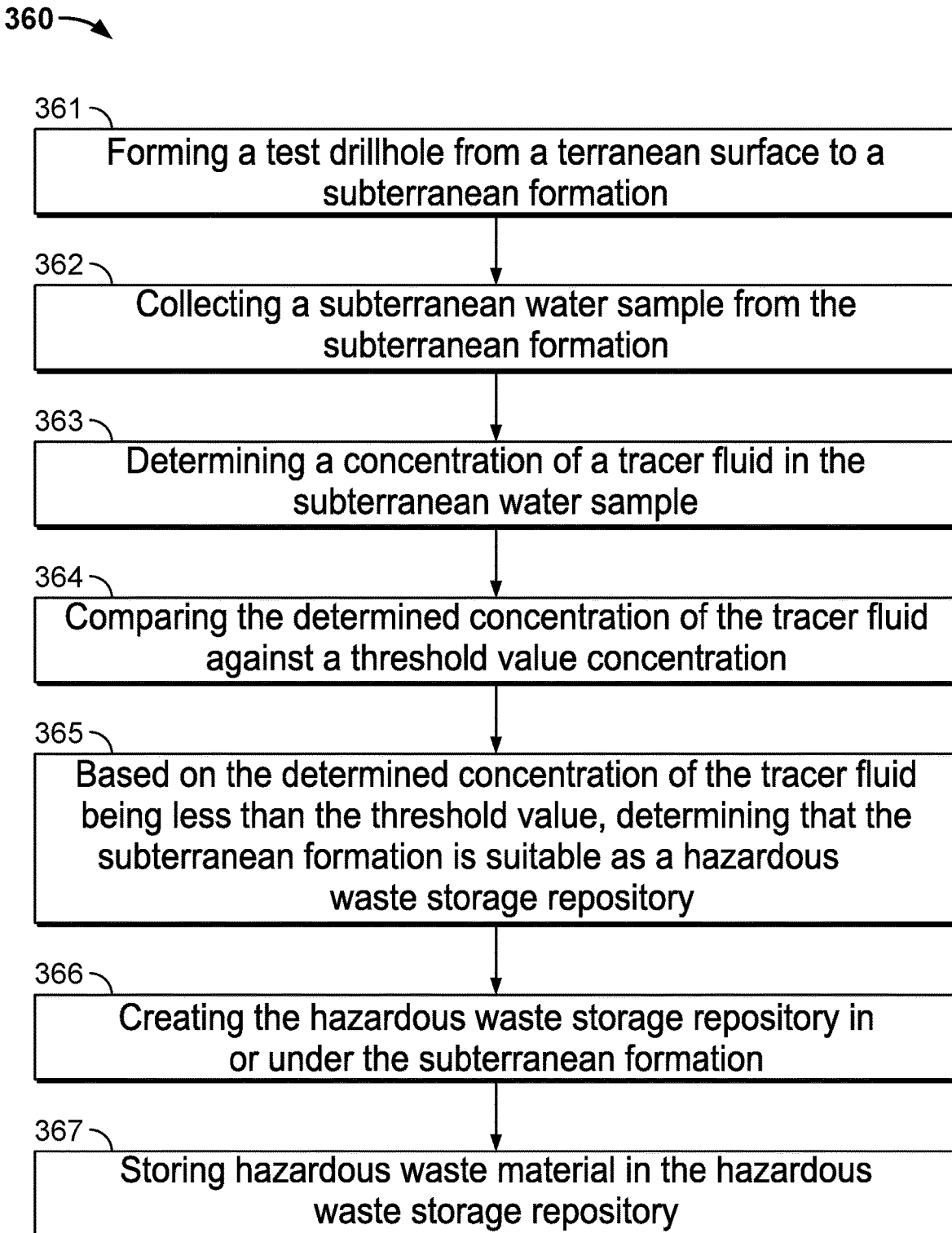

Turning now to FIG. 3E, this figure illustrates an example process 350 for determining the suitability of a subterranean formation as a hazardous waste repository by determining a secular equilibrium of one or more radioisotopes entrained in subterranean fluid (e.g., brine) within subterranean formations located at different vertical depths below a terranean surface to show mobility (or lack thereof) of the subterranean fluid. In some aspects, process 350 may be implemented by or with the system 100, including the fluid testing system 122.

For example, process 350 may analyze concentrations of natural isotopes of chlorine, iodine, and helium to put limits on the movement of subterranean fluid for the purpose of determining whether a particular subterranean formation (i.e., rock layer) is suitable as a hazardous waste repository for nuclear waste. Measurements of vertical profiles of these isotopes can determine the rate of the vertical flow of brines in the past. Such a measure may help determine whether the formation is suitable as a hazardous waste repository, e.g., if the rate is low enough to show that any mobile water/brine will not carry leaked nuclear waste toward a terranean surface.

As described, rock formations continue trace levels of U and Th. The primary components of these elements are radioactive with half-lives of 4.5 billion years (U-238) and 14 billion years (Th-232). These radioisotopes decay primarily by alpha emission, although there is a contribution from spontaneous fission of uranium isotopes 238 and 235. The radioactive decay of these isotopes has been constant over millions of years because of the long half-lives. The radioactive decays result in the constant rate of production of secondary radioisotopes.

In particular, U and Th lead to the constant production of chlorine-36 (Cl-36) and iodine-129 (I-129). The production of Cl-36 is complex process. The main production is a result of several steps: a uranium or thorium atom undergoes radioactive decay and emits an alpha particle. The alpha collides with another element (such as sodium or magnesium) present in the rock, and that often results in neutron emission. Finally, the neutron is absorbed by the stable isotope of chlorine, Cl-35, to produce the radioactive isotope Cl-36.

If Cl-36 were stable, its contribution would continue to build. However, it is radioactive with a half-life of 300,000 years. This decay is a primary source of depletion for Cl-36, and if none escapes a particular rock layer, the level of Cl-36 in that rock layer reaches a value referred to as "secular equilibrium" in which the production rate equals the decay rate. Secular equilibrium has been observed in water that has been trapped and isolated in deep subterranean formations. The observed level of Cl-36 in these brines is consistent, within about a 30% accuracy with the level expected by calculating the secular equilibrium level using the chemical and isotopic constitution of the rock and the water. The equilibrium value would shift, however, if there were a loss of Cl-36, for example, by fluid flow, i.e., "flow leakage."

Because of the hydrostatic equilibrium, any leaked brine is replaced by new brine. The shift could reduce the level of Cl-36 if the brine replacing the leaked component come from a rock with a lower production rate, either because uranium and thorium have reduced concentration, or because the neutron production is reduced from a lower concentration of neutron-production target atoms.

Process 350 may begin at step 351, which includes forming a test drillhole from a terranean surface through first and second rock layers (i.e., below a terranean surface). For example, test drillhole 104 may be formed (e.g., drilled) from the terranean surface 102 to and through subterranean formations 108 and 110. In some aspects, the first and second rock layers are located in adjacent (e.g., contacting) subterranean formations. In some aspects, the first and second rock layers may be separated by one or more intervening subterranean formations. In some aspects, the first and second rock layers may comprise a single rock type, but in distinct layers.

Process 350 may continue at step 352, which includes collecting a first water sample from the first rock layer at a first depth below the terranean surface. In some aspects, the water sample is brine. Alternatively, step 352 could include collecting a fluid sample. In some aspects, steps 351 and 351 may be replaced or avoided by identifying a previously collected water sample (e.g., liquid brine) from the first rock layer.

Process 350 may continue at step 353, which includes determining a first concentration of a particular radioisotope in the first water sample. In an example, the particular radioisotope is Cl-36. The concentration of Cl-36 may be directly measured from the first water sample. In alternative embodiments, the concentration of the Cl-36 in the first water sample may be performed with a direct measurement of the neutron flux in the first rock layer. For example, this can be done by running a neutron monitor (e.g., on a wireline, workstring, or other downhole conveyance) into the drillhole and detecting neutrons as a function of depth. These neutrons that create the Cl-36 create the measured flux value and the easily measured concentration of ordinary chlorine 35. Then, the concentration of Cl-36 at the first rock layer can be determined.

In other example embodiments, the radioisotope is I-129 and step 353 includes a determination of the concentration of I-129 in the first water sample. For example, this isotope is produced naturally in the formation in several ways, but at a depth of, e.g., 1 km the primary method is spontaneous fission of trace amounts of uranium 235 found in the formation. Iodine 129 has a half-life of about 16 million years, and it too reaches a secular equilibrium in which the uranium production matches the decay rate plus any flow loss.

In another example embodiment to evaluate the concentration of I-129, an iodine pulse can be evaluated if the evaluated formation is relatively young (e.g., less than 100 million years). This method is based on a pulse of iodine that is created when organic matter converts to hydrocarbons. This pulse derives from the very high concentration of iodine that exists in living matter, and which are released when the organic matter later produces hydrocarbons. Iodine is highly concentrated in oceanic organic matter by a factor of typically 4500, compared to the concentration in the water itself. The release of iodine during hydrocarbon maturation creates a pulse of iodine with a unique I-129/I-127 age signature. Iodine mobilized from such a deep organic layer can migrate upward through formations. The presence of the iodine pulse and its unique age can be used to constrain the age of the source formation for hydrocarbons. Since the I-129 concentration released during hydrocarbon production is generally much higher than background I-129 secular equilibrium concentrations, the movement of this old iodine pulse (which maintains I-129/I-127 age signature) can be determined and tracked upward through the rock layers.

In some example embodiments, the particular radioisotope is helium (He) and step 353 includes determining a concentration of He in the first water sample. For example, measurements of He gas as a function of depth can indicate the isolation of the formations for this very mobile element. Finding high travel velocity for helium does not necessarily mean that the radioisotopes Cl-36 and I-129 will move quickly through the rock, but if a low velocity is found for He, that may be an indication that the rock is very tight; chlorine and iodine will, in general, move at a lower velocity than will helium.

Helium may be created in the formation primarily from the alpha decay of uranium 238, uranium 235, and/or thorium 232. Since helium is stable, it does not decay, and the concentration depends primarily on the leakage rate. The production of helium can be calculated from the density of the uranium and thorium isotopes. Then the measured concentration of helium in step 353 gives a direct result for the stagnancy of the helium gas. In some instances, helium gas flow is expected to occur at a greater velocity than chlorine or iodine. Thus, if the flow velocity of the helium is found to be low, it may be an indicator of a high degree of isolation for the formation (e.g., fluid isolation from the terranean surface or groundwater sources).

Process 350 may continue at step 354, which includes collecting a second water sample from the second rock layer at a second depth below the terranean surface that is deeper than the first depth. In some aspects, the water sample is brine. Alternatively, step 354 could include collecting a fluid sample. In some aspects, step 354 may be replaced or avoided by identifying a previously collected water sample (e.g., liquid brine) from the second rock layer.

Process 350 may continue at step 355, which includes determining a second concentration of the particular radioisotope in the second water sample. Step 355, in some aspects, may be similar to step 353, but with the second water sample rather than the first. Thus, subsequent to step 355, there are two concentrations determined of the particular radioisotope at two different depths under the terranean surface.

Process 350 may continue at step 356, which includes determining that the particular radioisotope in the second water sample is at a secular equilibrium based on a ratio of the first and second concentrations of the particular radioisotope. In some aspects, a determination that the particular isotope is at secular equilibrium includes a determination that the ratio is at or close to 1. For example, in some aspects when the particular radioisotope is uranium, the secular equilibrium level can be calculated from the concentrations of uranium determined in steps 353 and 355. Any measured departure from the ratio of concentrations away from 1 may be an indication of flow of I-129 in the rock. Measurements of I-129 as a function of depth in the rock can determine if the I-129 is stagnant or whether it has been flowing at a velocity high enough to be of concern for human safety (e.g., high enough to reach the terranean surface or groundwater sources). Measurements of iodine concentration versus depth can be used to determine the concentration gradient of iodine across a number of geologic formations. The iodine gradient can be then used to estimate the diffusive or conductive flow velocity of iodine through the formations. Slow upward movement rates for iodine offer an indication that the rock strata can retain I-129 for long periods of time and may be suitable host formations for nuclear waste disposal in the hazardous waste repository.

In an example when the particular isotope is Cl-36, the ratio of concentrations of Cl-36 may be measured as a function of depth in steps 353 and 355. From this, it may be determined whether any variability seen is consistent with local (e.g., within one or between two or more formations) secular equilibrium. For example, if a subterranean layer above a proposed disposal formation (e.g., the formation into which the hazardous waste repository is formed in or with the directional drillhole) has low uranium and thorium content, and also shows a lower concentration of Cl-36 that is consistent with local secular equilibrium, then that fact provides strong evidence that Cl-36 is not leaking from the lower disposal layer into this upper layer, which provides an indicator of isolation (and thus suitability as a repository). On the other hand, if the observed Cl-36 level is higher than expected from secular equilibrium, than that is a possible indicator of leakage from below, indicating that the isolation of the lower layer is compromised by flow (and thus not suitable as a repository).

Process 350 may continue at step 357, which includes determining that the second rock layer formation is suitable as a hazardous waste repository based on the determination that the particular radioisotope is at secular equilibrium.

Process 350 may continue at step 358, which includes creating the hazardous waste storage repository (or at least initiating creation of the hazardous waste repository) in or under the second rock layer based on the determination of step 357. Process 350 may continue at step 359, which includes storing hazardous waste material in the hazardous waste storage repository. Example methods and processes for steps 358 and 359 are described with reference to FIGS. 2A-2B and 4.

In some embodiments, a characteristic of process 350 described here is that it puts limits on the flow velocity of Cl-36, rather than on the brine itself. When brine flows, the dissolved chlorine can interact with the rock and flow at a lower velocity. Thus, example embodiments of process 350 measure the flow of the chlorine (or other radioisotope), not that of the water. In some aspects, the movement of chlorine may be one of the more important considerations for safety of humans. The radioactive waste, itself, has Cl-36 as one of its most dangerous components; direct measurement of the Cl-36 flow is therefore more relevant than a measure of the water flow. In this considerations, embodiments of the present disclosure are closely tied to a potential requirement for safety, because it is the time that Cl-36 takes to reach the terranean surface and/or groundwater sources (e.g., potable water or otherwise) that has the greatest impact on public security. It is important that the travel velocity of Cl-36 is sufficiently slow that much of the radioactive material will have decayed (with its half-life of 300,000 years) prior to reaching the terranean surface or groundwater sources.

In some aspects, the selected subterranean zone (e.g., second rock layer) may include a "cap layer" at a depth between the terranean surface and a subterranean formation in which the hazardous material repository is located. In some aspects, the cap layer may prevent all or substantially all fluid flow therethrough. For instance, if there is a cap layer at which upward mobile helium is stopped, then that too can be taken as an indicator that disposal at a greater depth offers secure isolation (e.g., preventing radioactive waste from flowing from the hazardous material repository to the terranean surface). Since helium tends to be more mobile in formations than Cl-36 or I-129 or other long-lived radioisotopes, the presence of the cap layer may provide geologic isolation even if the second rock layer used for the repository includes upward flowpaths for leaked radioisotopes.

The present disclosure also describes a process for determining the suitability of a subterranean formation as a hazardous waste repository based on a measurement of a tracer fluid that was added to a drilling fluid used to form a wellbore, such as a test drillhole from which a subterranean fluid sample is collected. For example, turning to FIG. 3F, this figure illustrates an example process 360 for determining the suitability of a subterranean formation as a hazardous waste repository based on a measurement of the tracer fluid from a fluid sample from the subterranean formation. In some aspects, process 360 may be implemented by or with the system 100, including the fluid testing system 122.

The age of deep brines can be estimated by measuring the levels of carbon-14, chlorine-36, iodine-131, and/or other radioactive isotopes that are produced on the surface from cosmic rays. If the levels of one or more of these radioisotopes is lower at depth than it is for surface, then it may be concluded that surface water has not flowed downward to the rock formation that holds the brine for a period determined by the half-lives of the radioisotopes. "Surface water" in the present disclosure means water from a surface body of water or shallower aquifer that does not have an artificial increase of a radioactive isotope attributable to the atmospheric nuclear bomb testing that took place in the 1950s and 1960s.

For example, if the iodine-129 level in the subterranean water is less than half of the iodine-129 level observed in surface water, then it may be concluded that the brine is as least as old as the half-life of iodine-129, which is 16 million years. This dating may allow the conclusion that there has not been fluid communication between (e.g., mobile water flowing therebetween) the surface water and subterranean water for 16 million years, thus establishing the rock formation that holds the subterranean water as a suitable hazardous waste repository.

Subterranean water may suffer the risk of contamination. For example, subterranean water taken from deep wells may have been mixed with water used in the drilling process (e.g., water used in drilling mud). Such contamination typically leads to an underestimate of the age, since water used in drilling is typically surface water which has higher radioisotope content. Thus, in some aspects, the contamination of subterranean water with surface water in drilling mud may lead to a false determination that a subterranean formation that holds the contaminated brine is not suitable as a hazardous waste repository.

Process 360 may begin at step 361, which includes forming a test drillhole from a terranean surface to a subterranean formation. For example, test drillhole 104 may be formed (e.g., drilled) from the terranean surface 102 to the subterranean formation 110. Process 360 may continue at step 362, which includes collecting a subterranean water sample from the subterranean formation. In some aspects, the water sample is brine. Alternatively, step 362 could include collecting a subterranean fluid sample. In some aspects, steps 361 and 362 may be replaced or avoided by identifying a previously collected subterranean fluid sample (e.g., liquid brine).

Process 360 may continue at step 363, which includes determining a concentration of a tracer fluid in the subterranean water sample. For example, a drilling fluid (e.g., drilling mud) that is used in a drilling process for the test drillhole (or other drillhole or wellbore) may be mixed with a tracer, i.e., something that dissolves in the drilling fluid and does not precipitate or attach itself to the deep rock surfaces in the subterranean formation. Thus, the subterranean water sample may comprise a particular amount or concentration of the tracer. Examples of tracers include thiocyanate (often abbreviated SCN) and fluorobenzoic acid (FBA). Several dye tracers may include the property of ease of detectability (using a fluorometer), and the fact that very small amounts of dye (e.g., 1 part per billion) can be readily detected. Three potential dyes are rhodamine, pyranine, and sulforhodamine. Other tracers are possible.

Process 360 may continue at step 364, which includes comparing the determined concentration of the tracer fluid against a threshold value concentration. For example, a threshold value may be selected that shows that there is little to no tracer contamination in the subterranean water (or fluid) sample.

Process 360 may continue at step 365, which includes determining that the subterranean formation comprises a hazardous waste storage repository based on the determined concentration of the tracer fluid being less than the threshold value. For example, if the tracer is absent or low (e.g., below the predetermined threshold value), then it may be determined that contamination from surface water that is part of the drilling mud is absent or low. In such a determination, the subterranean formation may be determined as suitable as a hazardous waste (e.g., nuclear waste) repository.

In some aspects, process 360 may continue directly from step 365 to 366. In alternative aspects, other testing may be performed as part of process 360. For example, in some aspects, further testing, e.g., with an accelerator mass spectrometry (AMS) system or laser-based resonance ionization (which measures the radioisotope Kr-81 of one of the stable isotopes Kr-80, Kr-82, Kr-84, or Kr-86), may commence to determine the concentration of the radioactive isotope to determine an accurate age of the subterranean water sample. If the age is acceptable (thereby indicating that there has not been movement of surface water to the subterranean formation), then the formation may be confirmed as suitable as a hazardous waste (e.g., nuclear waste) repository.

Process 360 may continue at step 366, which includes creating the hazardous waste storage repository (or at least initiating creation of the hazardous waste repository) in or under the subterranean formation based on the determination of step 365. Process 360 may continue at step 367, which includes storing hazardous waste material in the hazardous waste storage repository. Example methods and processes for steps 366 and 367 are described with reference to FIGS. 2A-2B and 4.

Figure 2A:
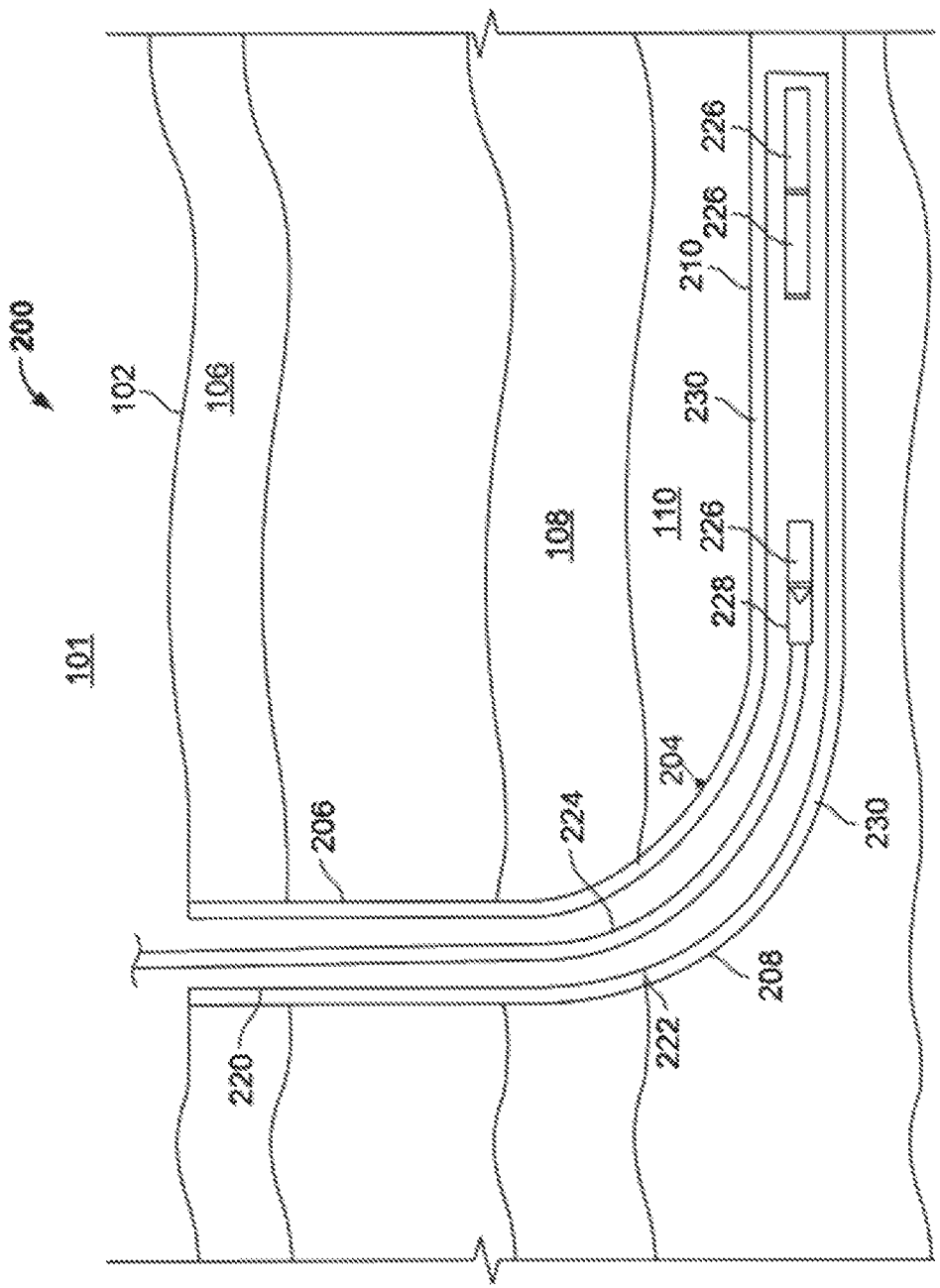
FIG. 2A is a schematic illustration of an example implementation of a hazardous waste material storage repository system during a deposit or retrieval operation according to the present disclosure.

FIG. 2A is a schematic illustration of example implementations of a hazardous waste material storage repository, e.g., a subterranean location for the long-term (e.g., tens, hundreds, or thousands of years or more) but retrievable safe and secure storage of hazardous waste material, during a deposit or retrieval operation according to the present disclosure. The hazardous waste material storage repository may be formed and operated, for example, subsequent to a determination that one or both of the subterranean formations 108 or 110 are suitable based on the radioactive isotope testing of the subterranean water as described in the present disclosure.

Turning to FIG. 2A, this figure illustrates an example hazardous waste material storage repository system 200 during a deposit (or retrieval, as described below) process, e.g., during deployment of one or more canisters of hazardous waste material in a subterranean formation. As illustrated, the hazardous waste material storage repository system 200 includes a drillhole 204 formed (e.g., drilled or otherwise) from the terranean surface 102 and through the subterranean layers 106, 108, and 110. In some aspects, the drillhole 204 may be the same as test drillhole 104 shown in FIG. 1. Alternatively, drillhole 204 may be an enlarged (e.g., reamed or re-drilled) version of test drillhole 104. Alternatively, the drillhole 204 may be a separate drillhole formed through the subterranean layers 106, 108, and into 110.

The illustrated drillhole 204 is a directional drillhole in this example of hazardous waste material storage repository system 200. For instance, the drillhole 204 includes an access drillhole 206 coupled to a radiussed or curved portion 208, which in turn is coupled to storage drillhole 210. In this example, the storage drillhole 210 is horizontal. Alternatively, curved portion 208 may be eliminated and storage drillhole 210 may be a vertical drillhole that couples to vertical access drillhole 204 to forma continuous, vertical drillhole. Alternatively, the curved portion 208 may differ from a 90-degree change in direction, in which case the storage drillhole 210 might be tilted.

The illustrated drillhole 204, in this example, has a surface casing 220 positioned and set around the drillhole 204 from the terranean surface 102 into a particular depth in the earth. For example, the surface casing 220 may be a relatively large-diameter tubular member (or string of members) set (e.g., cemented) around the drillhole 204 in a shallow formation. As used herein, "tubular" may refer to a member that has a circular cross-section, elliptical cross-section, or other shaped cross-section. For example, in this implementation of the hazardous waste material storage repository system 200, the surface casing 220 extends from the terranean surface through a surface layer 106. In some aspects, the surface casing 220 may isolate the drillhole 204 from surface water sources, and may also provide a hanging location for other casing strings to be installed in the drillhole 204.

As illustrated, a production casing 222 is positioned and set within the drillhole 204 downhole of the surface casing 220. Although termed a "production" casing, in this example, the casing 222 may or may not have been subject to hydrocarbon production operations. Thus, the casing 222 refers to and includes any form of tubular member that is placed in the drillhole 204 downhole of the surface casing 220. In some examples of the hazardous waste material storage repository system 200, the production casing 222 may begin at an end of the radiussed portion 108 and extend throughout the inclined portion 110. The casing 222 could also extend into the radiussed portion 108 and into the vertical portion 106.

As shown, cement 230 is positioned (e.g., pumped) around the casings 220 and 222 in an annulus between the casings 220 and 222 and the drillhole 204. The cement 230, for example, may secure the casings 220 and 222 (and any other casings or liners of the drillhole 204) through the subterranean formations under the terranean surface 102. In some aspects, the cement 230 may be installed along the entire length of the casings (e.g., casings 220 and 222 and any other casings), or the cement 230 could be used along certain portions of the casings if adequate for a particular drillhole 204. In some aspects the cement may be omitted altogether. The cement 230, if used, can also provide an additional layer of confinement for the hazardous waste material in canisters 226.

The storage drillhole portion 210 of the drillhole 204 includes a storage area in a distal part of the portion 210 into which hazardous waste material may be retrievably placed for long-term storage. For example, as shown, a work string 224 (e.g., tubing, coiled tubing, wireline, or otherwise) may be extended into the cased drillhole 204 to place one or more (three shown but there may be more or less) hazardous waste material canisters 226 into long-term, but in some aspects, retrievable, storage in the portion 210. For example, in the implementation shown in FIG. 2A, the work string 224 may include a downhole tool 228 that couples to the canister 226, and with each trip into the drillhole 204, the downhole tool 228 may deposit a particular hazardous waste material canister 226 in the storage drillhole portion 210.

The downhole tool 228 may couple to the canister 226 by, in some aspects, a threaded connection or other type of connection, such as a latched connection. In alternative aspects, the downhole tool 228 may couple to the canister 226 with an interlocking latch, such that rotation (or linear movement or electric or hydraulic switches) of the downhole tool 228 may latch to (or unlatch from) the canister 226. In alternative aspects, the downhole tool 228 may include one or more magnets (e.g., rare earth magnets, electromagnets, a combination thereof, or otherwise) which attractingly couple to the canister 226. In some examples, the canister 226 may also include one or more magnets (e.g., rare earth magnets, electromagnets, a combination thereof, or otherwise) of an opposite polarity as the magnets on the downhole tool 228. In some examples, the canister 226 may be made from or include a ferrous or other material attractable to the magnets of the downhole tool 228. Alternative techniques for moving the canisters 226 may also be used.

FIG. 2A also illustrates an example of a retrieval operation of hazardous waste material in the storage drillhole portion 210 of the drillhole 204. A retrieval operation may be the opposite of a deposit operation, such that the downhole tool 228 (e.g., a fishing tool) may be run into the drillhole 204, coupled to the last-deposited canister 226 (e.g., threadingly, latched, by magnet, or otherwise), and pull the canister 226 to the terranean surface 102. Multiple retrieval trips may be made by the downhole tool 228 in order to retrieve multiple canisters from the storage drillhole portion 210 of the drillhole 204.

Each canister 226 may enclose hazardous waste material. Such hazardous waste material, in some examples, may be biological or chemical waste or other biological or chemical hazardous waste material. In some examples, the hazardous waste material may include nuclear material, such as spent nuclear fuel recovered from a nuclear reactor (e.g., commercial power or test reactor) or defense nuclear material. For example, a gigawatt nuclear plant may produce 30 tons of spent nuclear fuel per year. The density of that fuel is typically close to 10 (10 gm/cm$^3$=10 kg/liter), so that the volume for a year of nuclear waste is about 3 m$^3$. Spent nuclear fuel, in the form of nuclear fuel pellets, may be taken from the reactor and not modified. Nuclear fuel pellet are solid, although they can contain and emit a variety of radioactive gases including tritium (13 year half-life), krypton-85 (10.8 year half-life), and carbon dioxide containing C-14 (5730 year half-life).

In some aspects, one or both of the subterranean formations 108 or 110 may contain any radioactive output (e.g., gases) therewithin, even if such output escapes the canisters 226. For example, one or both of the subterranean formations 108 or 110 may be shown to contain radioactive output based on the test results of the subterranean water testing as described with reference to FIGS. 1 and 3.

Other criteria in addition to the subterranean water testing as described herein may be used to determine that the subterranean formations 108 or 110 contain any radioactive output (e.g., gases) therewithin. For example, one or both of the subterranean formations 108 or 110 may be selected based on diffusion times of radioactive output through the formations 108 or 110. For example, a minimum diffusion time of radioactive output escaping the subterranean formations 108 or 110 may be set at, for example, fifty times a half-life for any particular component of the nuclear fuel pellets. Fifty half-lives as a minimum diffusion time would reduce an amount of radioactive output by a factor of $1\times10^{15}$. As another example, setting a minimum diffusion time to thirty half-lives would reduce an amount of radioactive output by a factor of one billion.

For example, plutonium-239 is often considered a dangerous waste product in spent nuclear fuel because of its long half-life of 24,200 years. For this isotope, 50 half-lives would be 1.2 million years. Plutonium-239 has low solubility in water, is not volatile, and as a solid, its diffusion time is exceedingly small (e.g., many millions of years) through a matrix of the rock formation that comprise the illustrated subterranean formations 108 or 110 (e.g., shale or other formation). The subterranean formations 108 or 110, for example comprised of shale, may offer the capability to have such isolation times (e.g., millions of years) as shown by the geological history of containing gaseous hydrocarbons (e.g., methane and otherwise) for several million years. In contrast, in conventional nuclear material storage methods, there was a danger that some plutonium might dissolve in a layer that comprised mobile ground water upon confinement escape.

In some aspects, the drillhole 204 may be formed for the primary purpose of long-term storage of hazardous waste materials. In alternative aspects, the drillhole 204 may have been previously formed for the primary purpose of hydrocarbon production (e.g., oil, gas). For example, one or both of subterranean formations 108 or 110 may be a hydrocarbon bearing formation from which hydrocarbons were produced into the drillhole 204 and to the terranean surface 102. In some aspects, the subterranean formations 108 or 110 may have been hydraulically fractured prior to hydrocarbon production. Further in some aspects, the production casing 222 may have been perforated prior to hydraulic fracturing. In such aspects, the production casing 222 may be patched (e.g., cemented) to repair any holes made from the perforating process prior to a deposit operation of hazardous waste material. In addition, any cracks or openings in the cement between the casing and the drillhole can also be filled at that time.

For example, in the case of spent nuclear fuel as a hazardous waste material, the drillhole may be formed at a particular location, e.g., near a nuclear power plant, as a new drillhole provided that the location also includes an appropriate subterranean formation 108 or 110, such as a shale formation. Alternatively, an existing well that has already produced shale gas, or one that was abandoned as "dry," (e.g., with sufficiently low organics that the gas in place is too low for commercial development), may be selected as the drillhole 204. In some aspects, prior hydraulic fracturing of the subterranean formations 108 or 110 through the drillhole 204 may make little difference in the hazardous waste material storage capability of the drillhole 204. But such a prior activity may also confirm the ability of one or both of the subterranean formations 108 or 110 to store gases and other fluids for millions of years. If, therefore, the hazardous waste material or output of the hazardous waste material (e.g., radioactive gasses or otherwise) were to escape from the canister 226 and enter the fractured formation of the subterranean formations 108 or 110, such fractures may allow that material to spread relatively rapidly over a distance comparable in size to that of the fractures. In some aspects, the drillhole 204 may have been drilled for a production of hydrocarbons, but production of such hydrocarbons had failed, e.g., because one or both of the subterranean formations 108 or 110 comprised a rock formation (e.g., shale or otherwise) that was too ductile and difficult to fracture for production, but was advantageously ductile for the long-term storage of hazardous waste material.

Figure 2B:
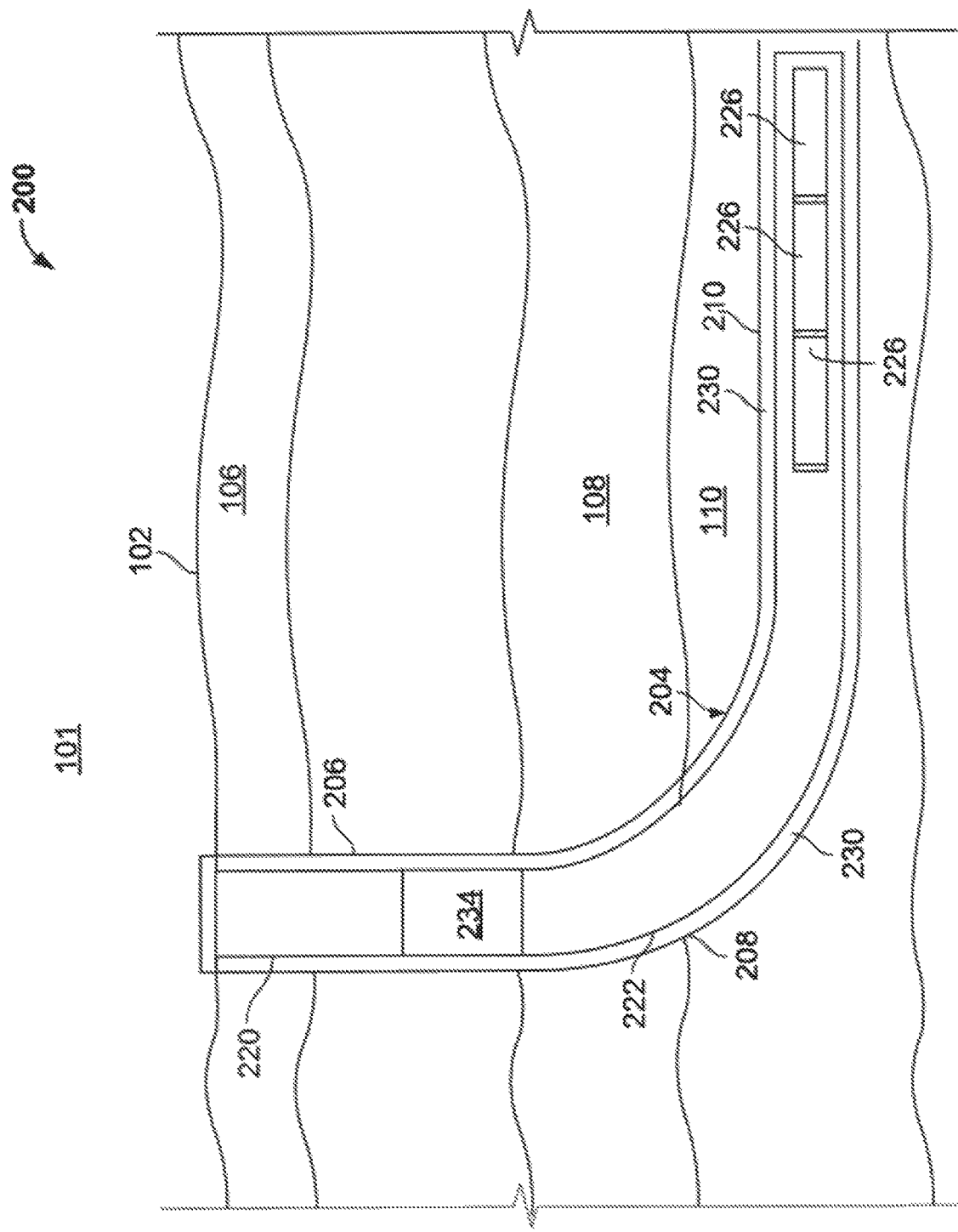
FIG. 2B is a schematic illustration of an example implementation of a hazardous waste material storage repository system during storage of hazardous waste material.

FIG. 2B is a schematic illustration of an example implementation of the hazardous waste material storage repository 200 during storage and monitoring operations according to the present disclosure. For example, FIG. 2B illustrates the hazardous waste material storage repository 200 in a long-term storage operation. One or more hazardous waste material canisters 226 are positioned in the storage drillhole portion 210 of the drillhole 204. A seal 234 is placed in the drillhole 204 between the location of the canisters 226 in the storage drillhole portion 210 and an opening of the access drillhole 206 at the terranean surface 102 (e.g., a well head). In this example, the seal 234 is placed at an uphole end of the curved portion 108. Alternatively, the seal 234 may be positioned at another location within the access drillhole 206, in the curved portion 208, or even within the storage drillhole portion 210 uphole of the canisters 226. In some aspects, the seal 234 may be placed at least deeper than any source of surface water, such as the surface water formation 106. In some aspects, the seal 234 may be formed substantially along an entire length of the access drillhole 206.

As illustrated, the seal 234 fluidly isolates the volume of the storage drillhole 110 that stores the canisters 226 from the opening of the access drillhole 206 at the terranean surface 102. Thus, any hazardous waste material (e.g., radioactive material) that does escape the canisters 226 may be sealed (e.g., such that liquid, gas, or solid hazardous waste material) does not escape the drillhole 104. The seal 234, in some aspects, may be a cement plug or other plug, that is positioned or formed in the drillhole 204. As another example, the seal 234 may be formed from one or more inflatable or otherwise expandable packers positioned in the drillhole 204. As another example, the seal 234 may be formed of a combination of rock and bentonite. As another example, the seal 234 may be formed from rock similar in composition to the rock found in nearby layers, such as clay-rich shale.

Prior to a retrieval operation (e.g., as discussed with reference to FIG. 2A), the seal 234 may be removed. For example, in the case of a cement or other permanently set seal 234, the seal 234 may be drilled through or otherwise milled away. In the case of semi-permanent or removable seals, such as packers, the seal 234 may be removed from the drillhole 204 through a conventional process as is known.

Monitoring operations may be performed during long-term storage of the canisters 226. For example, in some aspects, it may be advantageous or required to monitor one or more variables during long-term storage of the hazardous waste material in the canisters 226. In an example, a monitoring system includes one or more sensors placed in the drillhole 204 (e.g., within the storage drillhole 210) and communicably coupled to a monitoring control system through a cable (e.g., electrical, optical, hydraulic, or otherwise) or through a non-cable method (e.g. acoustic signals). The sensors may be placed outside of the casings, or even built into the casings before the casings are installed in the drillhole 204. Sensors could also be placed outside the casing.

The sensors may monitor one or more variables, such as, for example, radiation levels, temperature, pressure, presence of oxygen, a presence of water vapor, a presence of liquid water, acidity, seismic activity, or a combination thereof. Data values related to such variables may be transmitted along the cable to the monitoring control system. The monitoring control system, in turn, may record the data, determine trends in the data (e.g., rise of temperature, rise of radioactive levels), send data to other monitoring locations, such as national security or environmental center locations, and may further automatically recommend actions (e.g., retrieval of the canisters 226) based on such data or trends. For example, a rise in temperature or radioactive level in the drillhole 204 above a particular threshold level may trigger a retrieval recommendation, e.g., to ensure that the canisters 226 are not leaking radioactive material. In some aspects, there may be a one-to-one ratio of sensors to canisters 226. In alternative aspects, there may be multiple sensors per canister 226, or there may be fewer.

Figure 4:
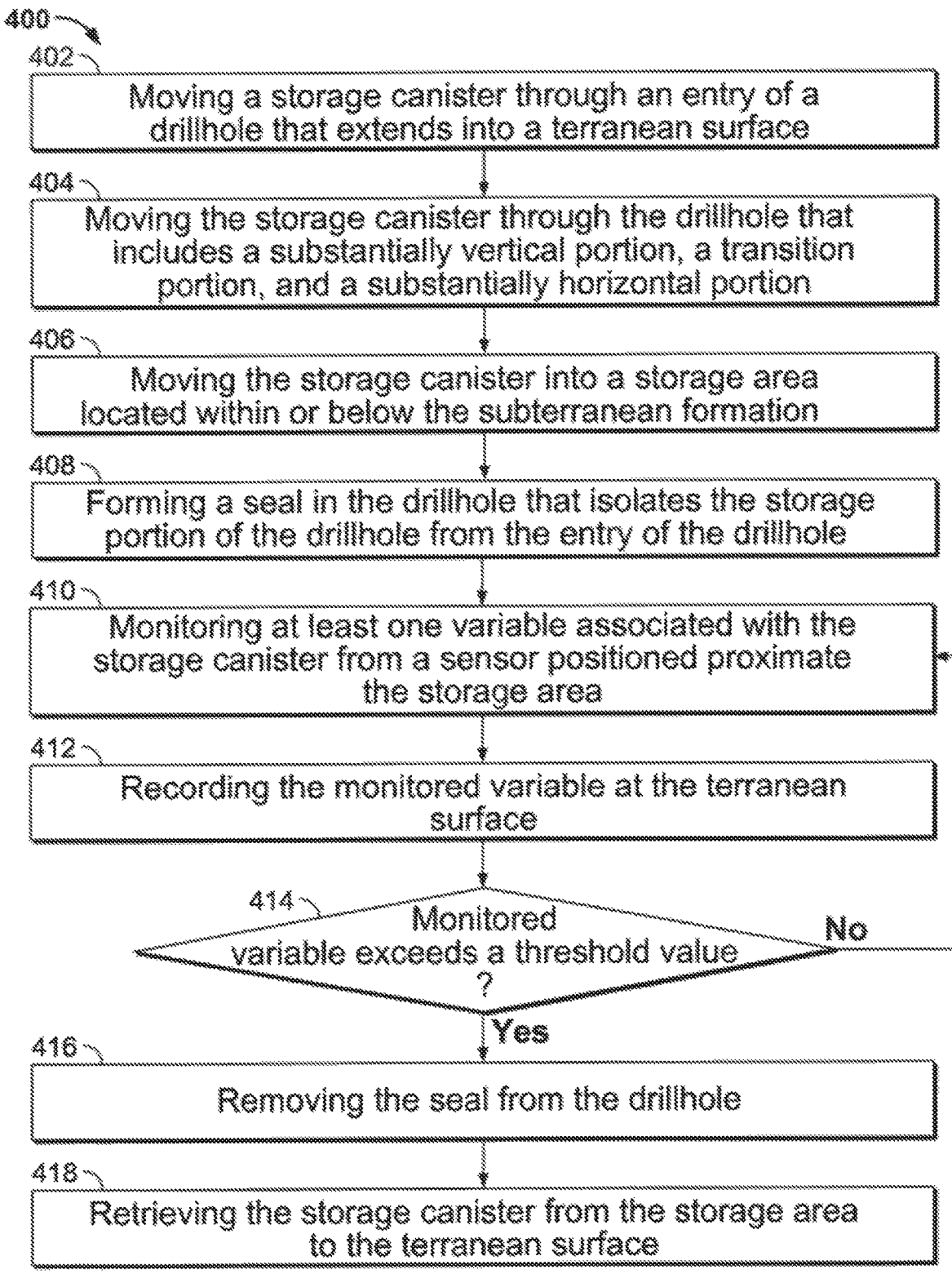
FIG. 4 is a flowchart that illustrates an example process for storing hazardous waste material in a subterranean formation from which water has been tested for a radioactive isotope concentration percentage.

FIG. 4 is a flowchart that illustrates an example implementation of a process 400 for storing hazardous waste material in a subterranean formation from which water has been tested for a radioactive isotope concentration percentage. Process 400 may begin with step 402, which includes moving a storage canister through an entry of a drillhole that extends into a terranean surface. The storage canister encloses a hazardous waste material, such as chemical, biological, or nuclear waste, or another hazardous waste material. In some aspects, the storage canister may be positioned in the entry directly from a mode of transportation (e.g., truck, train, rail, or otherwise) which brought the hazardous waste material to the site of the drillhole. In some aspects, a packaging of the hazardous waste material during transport is not removed for movement of the storage canister into the entry. In some aspects, such transport packaging is only removed as the storage canister fully enters the drillhole.

Process 400 may continue at step 404, which includes moving the storage canister through the drillhole that includes a substantially vertical portion, a transition portion, and a substantially horizontal portion. In some aspects, the drillhole is a directional, or slant drillhole. The storage canister may be moved through the drillhole in a variety of manners. For example, a tool string (e.g., tubular work string) or wireline may include a downhole tool that couples to the storage canister and moves (e.g., pushes) the storage canister from the entry to the horizontal portion of the drillhole. As another example, the storage canister may ride on rails installed in the drillhole, e.g., a cased drillhole. As yet another example, the storage canister may be moved through the drillhole with a drillhole tractor (e.g., motored or powered tractor). In another example, the tractor could be built as part of the storage canister. As yet a further example, the storage canister may be moved through the drillhole with a fluid (e.g., gas or liquid) circulated through the drillhole.

Process 400 may continue at step 406, which includes moving the storage canister into a storage area located within or below a subterranean formation which has been determined as suitable as a hazardous waste repository. For example, the horizontal portion of the drillhole may include or be coupled to the storage area and may be formed through the subterranean formation. In some aspects, the subterranean formation may include one or more geologic qualities (proven by one or more of the processes described herein) that provide for a fluidic seal (e.g., gas and liquid) against the escape of any hazardous waste material beyond the formation (e.g., vertically or horizontally).

Process 400 may continue at step 408, which includes forming a seal in the drillhole that isolates the storage portion of the drillhole from the entry of the drillhole. For example, once the storage canister is moved into the storage area (or after all storage canisters are moved into the storage area), a seal may be formed in the drillhole. The seal may be a cement plug, an inflatable seal (e.g., packer), a region containing a mixture of rock and bentonite, or other seal or combination of such seals. In some aspects, the seal is removable so as to facilitate a subsequent retrieval operation of the storage canister.

Process 400 may continue at step 410, which includes monitoring at least one variable associated with the storage canister from a sensor positioned proximate the storage area. The variable may include one or more of temperature, radioactivity, seismic activity, oxygen, water vapor, acidity, or other variable that indicates a presence of the hazardous waste material (e.g., within the drillhole, outside of the storage canister, in the rock formation, or otherwise). In some aspects, one or more sensors may be positioned in the drillhole, on or attached to the storage canister, within a casing installed in the drillhole, or in the rock formation proximate the drillhole. The sensors, in some aspects, may also be installed in a separate drillhole (e.g., another horizontal or vertical drillhole) apart from the storage area.

Process 400 may continue at step 412, which includes recording the monitored variable at the terranean surface. For example, variable data received at the one or more sensors may be transmitted (e.g., on a conductor or wirelessly) to a monitoring system at the terranean surface. The monitoring system may perform a variety of operations. For example, the monitoring system may record a history of one or more of the monitored variables. The monitoring system may provide trend analysis in the recorded variable data. As another example, the monitoring system may include one or more threshold limits for each of the monitored variables, and provide an indication when such threshold limits are exceeded.

Process 400 may continue at step 414, which includes determining whether the monitored variable exceeds a threshold value. For example, the one or more sensors may monitor radioactivity in the drillhole, e.g., an amount of radiation emitted by the hazardous waste material, whether in alpha or beta particles, gamma rays, x-rays, or neutrons. The sensors, for instance, may determine an amount of radioactivity, in units of measure of curie (Ci) and/or becquerel (Bq), rads, grays (Gy), or other units of radiation. If the amount of radioactivity does not exceed a threshold value that, for example, would indicate a large leak of hazardous nuclear material from the storage canister, then the process 400 may return to step 410.

If the determination is "yes," process 400 may continue at step 416, which includes removing the seal from the drillhole. For example, in some aspects, once a threshold value (or values) is exceeded, a retrieval operation may be initiated by removing the seal. In alternative aspects, exceeding of a threshold value may not automatically trigger a retrieval operation or removal of the drillhole seal. In some aspects, there may be multiple monitored variables, and a "yes" determination is only made if all monitored variables exceed their respective threshold values. Alternatively, a "yes" determination may be made if at least one monitored variable exceeds its respective threshold value.

Process 400 may continue at step 418, which includes retrieving the storage canister from the storage area to the terranean surface. For example, once the seal is removed (e.g., drilled through or removed to the terranean surface), the work string may be tripped into the drillhole to remove the storage canister for inspection, repair, or otherwise. In some aspects, rather than removing the seal from the drillhole to retrieve the storage canister, other remedial measures may be taken. For example, if the determination is "yes" in step 414, rather than recovering the hazardous waste material, a decision might be made to improve the seal. This could be done, for example, by injecting bentonite, a cement, or other sealant into the borehole to fill the space previously filled with gas.

Figure 5:
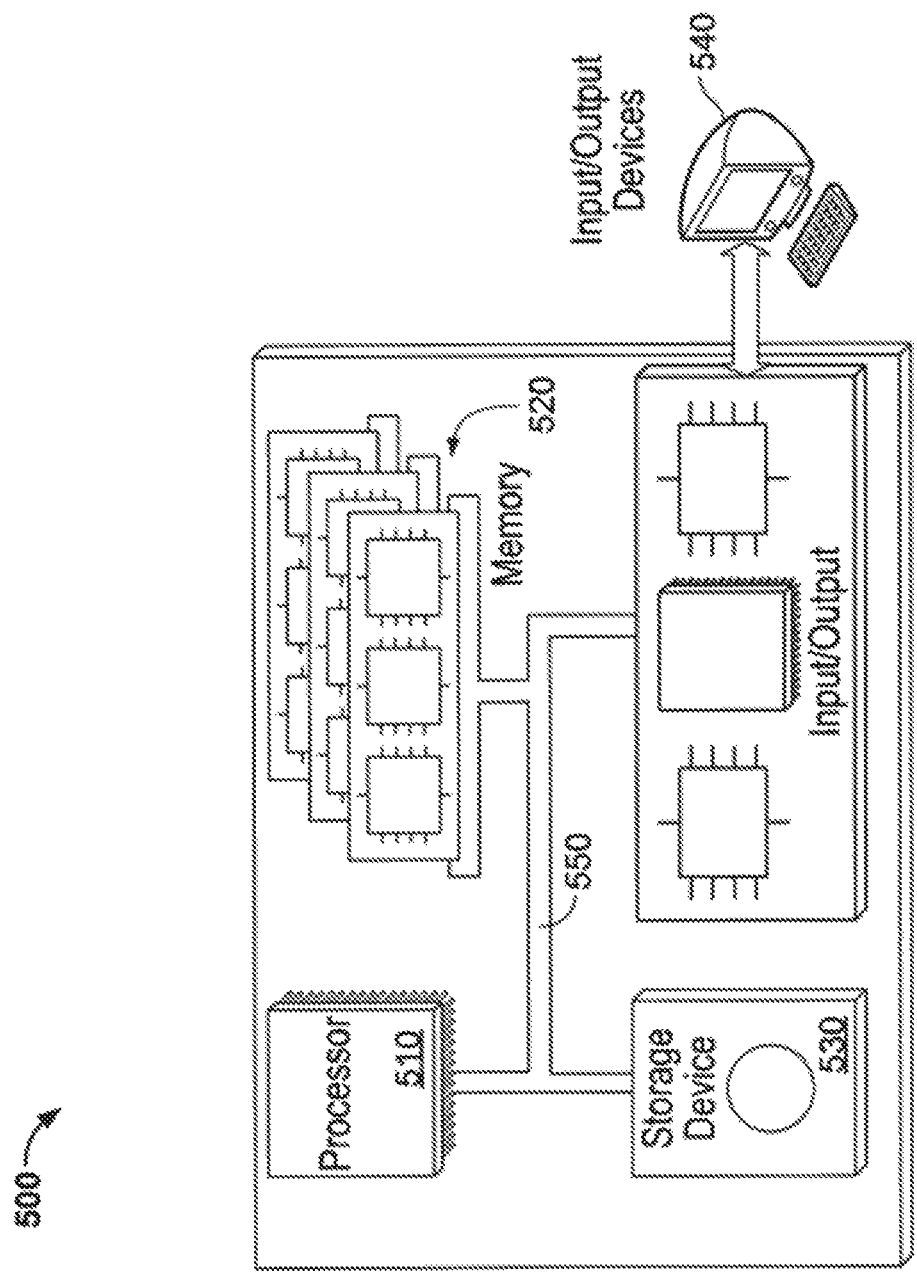
FIG. 5 is a schematic illustration of a controller or control system according to the present disclosure.

FIG. 5 is a schematic illustration of an example controller 500 (or control system) according to the present disclosure. For example, the controller 500 can be used for the operations described previously, for example as implementing all or some of the steps of any one of processes described in FIGS. 3A-3F and 4.

The controller 500 is intended to include various forms of digital computers, such as printed circuit boards (PCB), processors, digital circuitry, or otherwise. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 500 includes a processor 510, a memory 520, a storage device 530, and an input/output device 540. Each of the components 510, 520, 530, and 540 are interconnected using a system bus 550. The processor 510 is capable of processing instructions for execution within the controller 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the controller 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the controller 500. In one implementation, the storage device 530 is a computer-readable medium. In various different implementations, the storage device 530 may be a floppy disk device, a hard disk device, an optical disk device, a tape device, flash memory, a solid state device (SSD), or a combination thereof.

The input/output device 540 provides input/output operations for the controller 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, solid state drives (SSDs), and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A first example implementation according to the present disclosure includes a method that includes collecting a first water sample from a first rock layer at a first depth below a terranean surface; determining a first concentration of a particular radioisotope in the first water sample; collecting a second water sample from a second rock layer at a second depth below the terranean surface that is deeper than the first depth; determining a second concentration of the particular radioisotope in the second water sample; and based on the second concentration being greater than the first concentration by a specified percentage, determining that the second rock layer is suitable as a hazardous waste storage repository.

An aspect combinable with the first example implementation further includes, based on the determination that the second rock layer is suitable as the hazardous waste storage repository, forming an access drillhole from the terranean surface toward the second rock layer.

In another aspect combinable with any of the previous aspects of the first example implementation, the particular radioisotope comprises at least one of U-238, U-235, Th-232, K-40, I-129, or Cl-36.

In another aspect combinable with any of the previous aspects of the first example implementation, the specified percentage is at least 50 percent.

In another aspect combinable with any of the previous aspects of the first example implementation, collecting the first water sample comprises operating a downhole tool in a test drillhole to collect a first core sample from the first rock layer; retrieving the first core sample to the terranean surface; and removing the first water sample from the first core sample.

In another aspect combinable with any of the previous aspects of the first example implementation, collecting the second water sample comprises operating the downhole tool in the test drillhole to collect a second core sample from the second rock layer; retrieving the second core sample to the terranean surface; and removing the second water sample from the second core sample.

Another aspect combinable with any of the previous aspects of the first example implementation further includes forming the test drillhole from the terranean surface to the second rock layer.

In another aspect combinable with any of the previous aspects of the first example implementation, the test drillhole comprises a vertical drillhole.

In another aspect combinable with any of the previous aspects of the first example implementation, the second rock layer comprises a shale formation.

In another aspect combinable with any of the previous aspects of the first example implementation, the second rock layer comprises an impermeable layer.

In another aspect combinable with any of the previous aspects of the first example implementation, the second rock layer comprises a leakage barrier defined by a time constant for leakage of a hazardous waste material of 10,000 years or more.

In another aspect combinable with any of the previous aspects of the first example implementation, the second rock layer comprises a hydrocarbon or carbon dioxide bearing formation.

Another aspect combinable with any of the previous aspects of the first example implementation further includes initiating creation of the hazardous waste storage repository in or under the second rock layer.

In another aspect combinable with any of the previous aspects of the first example implementation, initiating creation of the hazardous waste storage repository in or under the second rock layer comprises forming an access drillhole from the terranean surface toward the second rock layer; and forming a storage drillhole coupled to the access drillhole in or under the second rock layer, the storage drillhole comprising a hazardous waste storage area.

In another aspect combinable with any of the previous aspects of the first example implementation, the access drillhole comprises a vertical drillhole.

In another aspect combinable with any of the previous aspects of the first example implementation, the access drillhole is the test drillhole comprises a portion of the access drillhole.

In another aspect combinable with any of the previous aspects of the first example implementation, the storage drillhole comprises a curved portion and a horizontal portion.

In another aspect combinable with any of the previous aspects of the first example implementation, the second rock layer comprises a thickness proximate the hazardous waste material storage area of at least about 200 feet.

In another aspect combinable with any of the previous aspects of the first example implementation, the second rock layer comprises a thickness proximate the hazardous waste material storage area that inhibits diffusion of a hazardous waste material through the second rock layer for an amount of time that is based on a half-life of the hazardous waste material.

Another aspect combinable with any of the previous aspects of the first example implementation further includes installing a casing in the access drillhole and the storage drillhole that extends from at or proximate the terranean surface, through the access drillhole and the storage drillhole, and into the hazardous waste material storage area of the storage drillhole.

Another aspect combinable with any of the previous aspects of the first example implementation further includes cementing the casing to the access drillhole and the storage drillhole.

Another aspect combinable with any of the previous aspects of the first example implementation further includes, subsequent to forming the access drillhole, producing hydrocarbon fluid from the second rock layer, through the access drillhole, and to the terranean surface.

Another aspect combinable with any of the previous aspects of the first example implementation further includes storing hazardous waste material in the hazardous waste storage area.

In another aspect combinable with any of the previous aspects of the first example implementation, storing hazardous waste material in the hazardous waste storage area comprises moving a storage canister through an entry of the access drillhole that extends into the terranean surface, the entry at least proximate the terranean surface, the storage canister comprising an inner cavity sized to enclose the hazardous waste material; moving the storage canister through the access drillhole and into the storage drillhole; and moving the storage canister through the storage drillhole to the hazardous waste storage area.

Another aspect combinable with any of the previous aspects of the first example implementation further includes forming a seal in at least one of the access drillhole or the storage drillhole that isolates the hazardous waste storage area from the entry of the access drillhole.

In another aspect combinable with any of the previous aspects of the first example implementation, the hazardous waste material comprises spent nuclear fuel.

In another aspect combinable with any of the previous aspects of the first example implementation, the storage canister comprises a connecting portion configured to couple to at least one of a downhole tool string or another storage canister.

Another aspect combinable with any of the previous aspects of the first example implementation further includes monitoring the hazardous waste material stored in the hazardous waste material storage area of the storage drillhole.

In another aspect combinable with any of the previous aspects of the first example implementation, monitoring the hazardous waste material stored in the hazardous waste material storage area of the storage drillhole comprises removing the seal; and retrieving the storage canister from the hazardous waste material storage area to the terranean surface.

In another aspect combinable with any of the previous aspects of the first example implementation, monitoring the hazardous waste material stored in the hazardous waste material storage area of the storage drillhole comprises monitoring at least one variable associated with the storage canister from a sensor positioned proximate the hazardous waste material storage area; and recording the monitored variable at the terranean surface.

In another aspect combinable with any of the previous aspects of the first example implementation, the monitored variable comprises at least one of radiation level, temperature, pressure, presence of oxygen, presence of water vapor, presence of liquid water, acidity, or seismic activity.

Another aspect combinable with any of the previous aspects of the first example implementation further includes, based on the monitored variable exceeding a threshold value, removing the seal; and retrieving the storage canister from the hazardous waste material storage drillhole portion to the terranean surface.

Another aspect combinable with any of the previous aspects of the first example implementation further includes, prior to collecting either of the first or second water samples, measuring a plurality of gamma rays output from at least one of the first or second rock layers; based on the measurement, collecting at least one of the first or second water samples.

A second example implementation according to the present disclosure includes a method that includes determining a first concentration of a particular radioisotope in a first water sample from a first rock layer at a first depth below a terranean surface; determining a second concentration of the particular radioisotope in a second water sample from a second rock layer at a second depth below the terranean surface that is deeper than the first depth; determining that the particular radioisotope in the second water sample is at a secular equilibrium based on a ratio of the first and second concentrations of the particular radioisotope; and based on the determination that the particular isotope in the second water sample is at the secular equilibrium, determining that the second rock layer is suitable as a hazardous waste storage repository.

An aspect combinable with the second example implementation further includes, based on the determination that the second rock layer is suitable as the hazardous waste storage repository, forming an access drillhole from the terranean surface toward the second rock layer.

In another aspect combinable with any of the previous aspects of the second example implementation, the particular radioisotope comprises at least one of I-129, He, or Cl-36.

In another aspect combinable with any of the previous aspects of the second example implementation, determining the first and second concentrations of the particular isotope comprises measuring a first neutron flux at a first depth of the first rock layer to determine the first concentration; and measuring a second neutron flux at a second depth of the second rock layer to determine the second concentration.

In another aspect combinable with any of the previous aspects of the second example implementation, determining that the particular radioisotope in the second water sample is at the secular equilibrium comprises comparing the measured first and second neutron fluxes.

Another aspect combinable with any of the previous aspects of the second example implementation further includes collecting the first water sample from a test drillhole formed into the first rock layer.

In another aspect combinable with any of the previous aspects of the second example implementation, collecting the first water sample comprises operating a downhole tool in the test drillhole to collect a first core sample from the first rock layer; retrieving the first core sample to the terranean surface; and removing the first water sample from the first core sample.

Another aspect combinable with any of the previous aspects of the second example implementation further includes collecting the second water sample from the test drillhole formed into the second rock layer.

In another aspect combinable with any of the previous aspects of the second example implementation, collecting the second water sample comprises operating the downhole tool in the test drillhole to collect a second core sample from the second rock layer; retrieving the second core sample to the terranean surface; and removing the second water sample from the second core sample.

Another aspect combinable with any of the previous aspects of the second example implementation further includes forming the test drillhole from the terranean surface to the second rock layer.

In another aspect combinable with any of the previous aspects of the second example implementation, the test drillhole comprises a vertical drillhole.

In another aspect combinable with any of the previous aspects of the second example implementation, the second rock layer comprises a shale formation.

In another aspect combinable with any of the previous aspects of the second example implementation, the second rock layer comprises an impermeable layer.

In another aspect combinable with any of the previous aspects of the second example implementation, the second rock layer comprises a leakage barrier defined by a time constant for leakage of a hazardous waste material of 10,000 years or more.

In another aspect combinable with any of the previous aspects of the second example implementation, the second rock layer comprises a hydrocarbon or carbon dioxide bearing formation.

Another aspect combinable with any of the previous aspects of the second example implementation further includes initiating creation of the hazardous waste storage repository in or under the second rock layer.

In another aspect combinable with any of the previous aspects of the second example implementation, initiating creation of the hazardous waste storage repository in or under the second rock layer comprises forming an access drillhole from the terranean surface toward the second rock layer; and forming a storage drillhole coupled to the access drillhole in or under the second rock layer. The storage drillhole includes a hazardous waste storage area.

In another aspect combinable with any of the previous aspects of the second example implementation, the access drillhole comprises a vertical drillhole.

In another aspect combinable with any of the previous aspects of the second example implementation, the access drillhole is the test drillhole comprises a portion of the access drillhole.

In another aspect combinable with any of the previous aspects of the second example implementation, the storage drillhole comprises a curved portion and a horizontal portion.

In another aspect combinable with any of the previous aspects of the second example implementation, the second rock layer comprises a thickness proximate the hazardous waste material storage area of at least about 200 feet.

In another aspect combinable with any of the previous aspects of the second example implementation, the second rock layer comprises a thickness proximate the hazardous waste material storage area that inhibits diffusion of a hazardous waste material through the second rock layer for an amount of time that is based on a half-life of the hazardous waste material.

Another aspect combinable with any of the previous aspects of the second example implementation further includes installing a casing in the access drillhole and the storage drillhole that extends from at or proximate the terranean surface, through the access drillhole and the storage drillhole, and into the hazardous waste material storage area of the storage drillhole.

Another aspect combinable with any of the previous aspects of the second example implementation further includes cementing the casing to the access drillhole and the storage drillhole.

Another aspect combinable with any of the previous aspects of the second example implementation further includes, subsequent to forming the access drillhole, producing hydrocarbon fluid from the second rock layer, through the access drillhole, and to the terranean surface.

Another aspect combinable with any of the previous aspects of the second example implementation further includes storing hazardous waste material in the hazardous waste storage area.

In another aspect combinable with any of the previous aspects of the second example implementation, storing hazardous waste material in the hazardous waste storage area comprises moving a storage canister through an entry of the access drillhole that extends into the terranean surface, the entry at least proximate the terranean surface, the storage canister comprising an inner cavity sized to enclose the hazardous waste material; moving the storage canister through the access drillhole and into the storage drillhole; and moving the storage canister through the storage drillhole to the hazardous waste storage area.

Another aspect combinable with any of the previous aspects of the second example implementation further includes forming a seal in at least one of the access drillhole or the storage drillhole that isolates the hazardous waste storage area from the entry of the access drillhole.

In another aspect combinable with any of the previous aspects of the second example implementation, the hazardous waste material comprises spent nuclear fuel.

In another aspect combinable with any of the previous aspects of the second example implementation, the storage canister comprises a connecting portion configured to couple to at least one of a downhole tool string or another storage canister.

Another aspect combinable with any of the previous aspects of the second example implementation further includes comprising monitoring the hazardous waste material stored in the hazardous waste material storage area of the storage drillhole.

In another aspect combinable with any of the previous aspects of the second example implementation, monitoring the hazardous waste material stored in the hazardous waste material storage area of the storage drillhole comprises removing the seal; and retrieving the storage canister from the hazardous waste material storage area to the terranean surface.

In another aspect combinable with any of the previous aspects of the second example implementation, monitoring the hazardous waste material stored in the hazardous waste material storage area of the storage drillhole comprises monitoring at least one variable associated with the storage canister from a sensor positioned proximate the hazardous waste material storage area; and recording the monitored variable at the terranean surface.

In another aspect combinable with any of the previous aspects of the second example implementation, the monitored variable comprises at least one of radiation level, temperature, pressure, presence of oxygen, presence of water vapor, presence of liquid water, acidity, or seismic activity.

Another aspect combinable with any of the previous aspects of the second example implementation further includes, based on the monitored variable exceeding a threshold value, removing the seal; and retrieving the storage canister from the hazardous waste material storage drillhole portion to the terranean surface.

In another aspect combinable with any of the previous aspects of the second example implementation, the secular equilibrium comprises a ratio in which a production rate of the particular isotope equals a decay rate of the particular isotope.

Another aspect combinable with any of the previous aspects of the second example implementation further includes determining a flow velocity of the particular radioisotope between the second and first rock layers based on the ratio of the first and second concentrations of the particular radioisotope.

In another aspect combinable with any of the previous aspects of the second example implementation, determining the flow velocity of the particular radioisotope between the second and first rock layers comprises determining the flow velocity of the particular radioisotope between the second and first rock layers independent of a flow velocity of a brine flow between the second and first rock layers that includes the particular radioisotope.

A third example implementation according to the present disclosure includes a method including collecting, from a test drillhole formed from a terranean surface to a subterranean formation, a subterranean water sample from the subterranean formation; determining a concentration of a tracer fluid in the subterranean water sample, the tracer fluid comprising a fluid mixed into a drilling fluid used in a drilling process to form the test drillhole; comparing the determined concentration of the tracer fluid against a threshold value concentration; and based on the determined concentration of the tracer fluid being less than the threshold value, determining that the subterranean formation comprises a hazardous waste storage repository.

An aspect combinable with the third example implementation further includes, subsequent to the determination that the determined concentration of the tracer fluid is less than the threshold value, performing a low level radioisotope dating technique.

In another aspect combinable with any of the previous aspects of the third example implementation, performing the low level radioisotope dating technique comprises determining, with an accelerator mass spectrometry (AMS) system, a concentration of a radioactive isotope of an element in the subterranean water sample relative to a stable isotope of the element in the subterranean water sample; comparing the determined concentration of the radioactive isotope of the element in the subterranean water sample with a concentration of the radioactive isotope of the element in a surface water sample relative to the stable isotope of the element in the surface water sample; and based on the determined concentration of the radioactive isotope in the subterranean water sample being a specified percentage of the concentration of the radioactive isotope in the surface water sample, determining that the subterranean formation comprises a hazardous waste storage repository.

In another aspect combinable with any of the previous aspects of the third example implementation, the radioactive isotope is carbon-14 ($^{14}C$) and the stable isotope is $^{12}C$ or $^{13}C$; the radioactive isotope is chlorine-36 ($^{36}Cl$) and the stable isotope is $^{35}Cl$; the radioactive isotope is iodine-129 ($^{129}I$) and the stable isotope is $^{127}I$; the radioactive isotope is beryllium-10 ($^{10}Be$) and the stable isotope is $^{9}Be$; or the radioactive isotope is aluminum-26 ($^{26}Al$) and the stable isotope is $^{27}Al$.

In another aspect combinable with any of the previous aspects of the third example implementation, the specified percentage is less than 50 percent.

In another aspect combinable with any of the previous aspects of the third example implementation, performing the low level radioisotope dating technique comprises determining, with a laser-based resonance ionization system, a concentration of a radioactive isotope of an element in the subterranean water sample relative to a stable isotope of the element in the subterranean water sample; comparing the determined concentration of the radioactive isotope of the element in the subterranean water sample with a concentration of the radioactive isotope of the element in a surface water sample relative to the stable isotope of the element in the surface water sample; and based on the determined concentration of the radioactive isotope in the subterranean water sample being a specified percentage of the concentration of the radioactive isotope in the surface water sample, determining that the subterranean formation comprises a hazardous waste storage repository.

In another aspect combinable with any of the previous aspects of the third example implementation, the radioactive isotope is Kr-81 and the stable isotope is at least one of Kr-80, Kr-82, Kr-84, or Kr-86.

In another aspect combinable with any of the previous aspects of the third example implementation, the surface water source comprises at least one of an aquifer or a water source at the terranean surface in contact with the earth's atmosphere.

In another aspect combinable with any of the previous aspects of the third example implementation, the tracer fluid comprises at least one of thiocyanate, fluorobenzoic acid, rhodamine, pyranine, or sulforhodamine.

In another aspect combinable with any of the previous aspects of the third example implementation, the tracer fluid comprises a dye.

In another aspect combinable with any of the previous aspects of the third example implementation, the tracer fluid comprises a fluid that comprises properties of low absorption in rock and ease of detectability.

In another aspect combinable with any of the previous aspects of the third example implementation, the hazardous waste storage repository is configured to store nuclear waste.

In another aspect combinable with any of the previous aspects of the third example implementation, the nuclear waste comprises spent nuclear fuel.

A fourth example implementation according to the present disclosure includes a system that includes a subterranean water sample collection apparatus configured to collect, from a test drillhole formed from a terranean surface to a subterranean formation, a subterranean water sample from the subterranean formation; and a subterranean water sample test apparatus. The subterranean water sample test apparatus is configured to determine a concentration of a tracer fluid in the subterranean water sample, the tracer fluid comprising a fluid mixed into a drilling fluid used in a drilling process to form the test drillhole; compare the determined concentration of the tracer fluid against a threshold value concentration; and based on the determined concentration of the tracer fluid being less than the threshold value, provide an indication that the subterranean formation comprises a hazardous waste storage repository.

An aspect combinable with the fourth example implementation further includes an accelerator mass spectrometry (AMS) system configured to subsequent to the determination that the determined concentration of the tracer fluid is less than the threshold value, determine a concentration of a radioactive isotope of an element in the subterranean water sample relative to a stable isotope of the element in the subterranean water sample; compare the determined concentration of the radioactive isotope of the element in the subterranean water sample with a concentration of the radioactive isotope of the element in a surface water sample relative to the stable isotope of the element in the surface water sample; and based on the determined concentration of the radioactive isotope in the subterranean water sample being a specified percentage of the concentration of the radioactive isotope in the surface water sample, provide an indication that the subterranean formation comprises a hazardous waste storage repository.

In another aspect combinable with any of the previous aspects of the fourth example implementation, the radioactive isotope is carbon-14 ($^{14}C$) and the stable isotope is $^{12}C$ or $^{13}C$; the radioactive isotope is chlorine-36 ($^{36}Cl$) and the stable isotope is $^{35}Cl$; the radioactive isotope is iodine-129 ($^{129}I$) and the stable isotope is $^{127}I$; the radioactive isotope is beryllium-10 ($^{10}Be$) and the stable isotope is $^{9}Be$; or the radioactive isotope is aluminum-26 ($^{26}Al$) and the stable isotope is $^{27}Al$.

In another aspect combinable with any of the previous aspects of the fourth example implementation, the specified percentage is less than 50 percent.

Another aspect combinable with any of the previous aspects of the fourth example implementation further includes a laser-based resonance ionization system configured to subsequent to the determination that the determined concentration of the tracer fluid is less than the threshold value, determine a concentration of a radioactive isotope of an element in the subterranean water sample relative to a stable isotope of the element in the subterranean water sample; compare the determined concentration of the radioactive isotope of the element in the subterranean water sample with a concentration of the radioactive isotope of the element in a surface water sample relative to the stable isotope of the element in the surface water sample; and based on the determined concentration of the radioactive isotope in the subterranean water sample being a specified percentage of the concentration of the radioactive isotope in the surface water sample, provide an indication that the subterranean formation comprises a hazardous waste storage repository.

In another aspect combinable with any of the previous aspects of the fourth example implementation, the radioactive isotope is Kr-81 and the stable isotope is at least one of Kr-80, Kr-82, Kr-84, or Kr-86.

In another aspect combinable with any of the previous aspects of the fourth example implementation, the surface water source comprises at least one of an aquifer or a water source at the terranean surface in contact with the earth's atmosphere.

In another aspect combinable with any of the previous aspects of the fourth example implementation, the tracer fluid comprises at least one of thiocyanate, fluorobenzoic acid, rhodamine, pyranine, or sulforhodamine.

In another aspect combinable with any of the previous aspects of the fourth example implementation, the tracer fluid comprises a dye.

In another aspect combinable with any of the previous aspects of the fourth example implementation, the tracer fluid comprises a fluid that comprises properties of low absorption in rock and ease of detectability.

In another aspect combinable with any of the previous aspects of the fourth example implementation, the hazardous waste storage repository is configured to store nuclear waste.

In another aspect combinable with any of the previous aspects of the fourth example implementation, the nuclear waste comprises spent nuclear fuel.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:
1. A method, comprising:
 determining a neutron flux of a first isotope in a subterranean formation;
 calculating, based at least in part on the determined neutron flux of the first isotope, a predicted production rate of a second isotope in the subterranean formation;
 calculating a first ratio of the predicted production rate of the second isotope relative to a theoretical production rate of a stable form of the second isotope;
 measuring respective concentrations of the second isotope and the stable form of the second isotope in a subterranean water sample from the subterranean formation;
 calculating a second ratio of the measured concentration of the second isotope relative to the measured concentration of the stable form of the second isotope;
 based on a comparison of the first and second ratios, determining that the subterranean formation is suitable as a hazardous waste repository; and
 based on the determination that the subterranean formation is suitable as the hazardous waste repository, forming an access drillhole from the terranean surface toward the subterranean formation.

2. The method of claim 1, wherein the first isotope comprises a first half-life, and the second isotope comprises a second half-life longer than the first half-life.

3. The method of claim 1, wherein the first isotope comprises Ar-39, Fe-59, Co-60, Ni-63, Kr-85, Ni-63, or C-14.

4. The method of claim 1, wherein the second isotope comprises Cl-36.

5. The method of claim 4, wherein the stable form of the second isotope comprises Cl-35.

6. The method of claim 1, further comprising comparing the first and second ratios to determine that the first and second ratios are equal.

7. The method of claim 1, wherein determining the neutron flux of the first isotope in the subterranean formation comprises determining the neutron flux of the first isotope based on a bulk rock chemistry of the subterranean formation.

8. The method of claim 7, wherein the bulk rock chemistry comprises an amount of uranium or thorium, or both, per unit volume of the subterranean formation.

9. The method of claim 1, further comprising collecting the water sample from a drillhole formed into the subterranean formation.

10. The method of claim 9, wherein collecting the water sample comprises:
 operating a downhole tool in the drillhole to collect a core sample from the subterranean formation;
 retrieving the core sample to the terranean surface; and
 removing the water sample from the core sample.

11. The method of claim 9, further comprising forming the drillhole from the terranean surface to the subterranean formation.

12. The method of claim 9, wherein the drillhole comprises a portion of the access drillhole.

13. The method of claim 1, further comprising initiating creation of the hazardous waste repository in or under the subterranean formation.

14. The method of claim 13, wherein initiating creation of the hazardous waste repository in or under the subterranean formation comprises:
 forming a storage drillhole coupled to the access drillhole in or under the subterranean formation, the storage drillhole comprising a hazardous waste storage area.

15. The method of claim 14, wherein the storage drillhole comprises a curved portion and a horizontal portion.

16. The method of claim 15, further comprising storing hazardous waste material in the hazardous waste storage area.

17. The method of claim 16, wherein storing hazardous waste material in the hazardous waste storage area comprises:
 moving a storage canister through an entry of the access drillhole that extends into the terranean surface, the entry at least proximate the terranean surface, the storage canister including an inner cavity sized to enclose the hazardous waste material;
 moving the storage canister through the access drillhole and into the storage drillhole; and
 moving the storage canister through the storage drillhole to the hazardous waste storage area.

18. The method of claim 17, further comprising forming a seal in at least one of the access drillhole or the storage drillhole that isolates the hazardous waste storage area from the entry of the access drillhole subsequent to moving the storage canister through the storage drillhole to the hazardous waste storage area.

19. The method of claim 1, wherein the access drillhole comprises a vertical drillhole.

20. The method of claim 1, further comprising:
monitoring at least one variable associated with the storage canister or the hazardous waste material from a sensor positioned proximate the hazardous waste storage area;
based on the monitored variable exceeding a threshold value:
removing the seal, and
retrieving the storage canister from the hazardous waste storage area to the terranean surface.

* * * * *